(12) United States Patent
Mehl et al.

(10) Patent No.: US 10,932,838 B2
(45) Date of Patent: Mar. 2, 2021

(54) BONE COMPRESSION SCREWS

(71) Applicant: Life Spine, Inc., Huntley, IL (US)

(72) Inventors: David T. Mehl, Streamwood, IL (US); Daniel P. Predick, West Lafayette, IN (US); Michael S. Butler, St. Charles, IL (US)

(73) Assignee: LIFE SPINE, INC., Huntley, IL (US)

( * ) Notice: Subject to any disclaimer, the term of this patent is extended or adjusted under 35 U.S.C. 154(b) by 874 days.

(21) Appl. No.: 15/089,558

(22) Filed: Apr. 3, 2016

(65) Prior Publication Data

US 2016/0287301 A1 Oct. 6, 2016

Related U.S. Application Data

(60) Provisional application No. 62/142,529, filed on Apr. 3, 2015.

(51) Int. Cl.
| | | |
|---|---|---|
| *A61B 17/04* | (2006.01) | |
| *A61B 17/86* | (2006.01) | |
| *A61F 2/08* | (2006.01) | |

(52) U.S. Cl.
CPC .......... *A61B 17/863* (2013.01); *A61B 17/864* (2013.01); *A61B 17/8685* (2013.01)

(58) Field of Classification Search
None
See application file for complete search history.

(56) References Cited

U.S. PATENT DOCUMENTS

| | | | | |
|---|---|---|---|---|
| 2004/0210227 A1* | 10/2004 | Trail | ................... | A61B 17/863 606/916 |
| 2012/0130433 A1* | 5/2012 | Huebner | .............. | A61B 17/863 606/300 |
| 2013/0238036 A1* | 9/2013 | Sinha | ..................... | A61B 17/68 606/304 |
| 2013/0338722 A1* | 12/2013 | Yalizis | .................. | A61B 17/68 606/312 |

* cited by examiner

*Primary Examiner* — Sameh R Boles
(74) *Attorney, Agent, or Firm* — Foley & Lardner LLP

(57) ABSTRACT

Bone compression screws are characterized by a two-piece compression screw assembly comprising a screw component and a sleeve component. The screw component has external male bone screw threading at a distal end, external male machine screw threading on a proximal end, and a smooth shank between the threaded distal and proximal ends. The screw component may be solid, cannulated, slotted, fenestrated, fluted, helically fluted, or any combination thereof. The sleeve component has external male bone screw threading with a pitch that can be equal to, smaller than, or greater than the thread pitch of the screw component, an internal bore extending from a proximal end of the sleeve component to the distal end of the sleeve component and sized for reception over the proximal end of the screw component. Internal female machine screw threading is configured to mate with the external male machine screw threading of the screw component.

5 Claims, 29 Drawing Sheets

BONE COMPRESSION SCREWS

CROSS-REFERENCE TO RELATED APPLICATIONS

This U.S. non-provisional patent application claims the benefit of and/or priority under 35 U.S.C. § 119(e) to U.S. provisional patent application Ser. No. 62/142,529 filed Apr. 3, 2015 titled "Bone Compression Screws," the entire contents of which is specifically incorporated herein by reference.

FIELD OF THE INVENTION

The present invention relates to implants for fixation of human bones, and more particularly, to compression screws for stabilizing and compressing human bones such as, but not limited to, in the sacroiliac.

BACKGROUND

Compression screws, both headless and headed, are routinely used for fixing or mending bones and bone joints of the body. Particularly, and without being exhaustive, compression screws of various lengths are used for fixation of intra-articular and extra-articular fractures, avulsions, non-unions, arthrodesis, osteotomies, reconstruction of various bones, joint fixation and the like. A fundamental property of compression screws is the amount of compression the screw achieves. Typically, the greater the amount of compression the screw can provide the better, as the bone, bones or bone joints will strongly mend when tightly held together.

Once installed, it would be desirable that the bone compression screw does not rotate or otherwise shift in position and/or orientation. Additionally, it would be desirable if the bone compression screw could aid in the bone mending process.

In view of the above, it is apparent that improvements can be made in bone compression screws. As such, it is desirable to have bone compression screws that overcome the deficiencies of the prior art. It is also desirable to have bone compression screws that are not susceptible to shifts in position once installed.

SUMMARY OF THE INVENTION

The present invention is a bone compression screw and method of use for compressing a bone joint, bone fracture, or other (collectively, "boney anatomy") together. The bone compression screw is characterized by a two-piece compression screw assembly comprising a screw component and a sleeve component.

The screw component is characterized by a body having external male bone screw threading at a distal end of the body, external male machine screw threading on a proximal end of the body, and a smooth shank between the threaded distal end of the body and the threaded proximal end of the body.

The screw component may be solid, cannulated, slotted, non-slotted, fenestrated, non-fenestrated, or any combination thereof, for bone graft. The screw component may also include one or more drive features at its distal end, as well as one or more distal thread features. The screw component may also incorporate helical flute geometries that function as bone cutting flutes that self-harvest bone graft that is collected by graft windows. The graft windows may be slotted (perpendicular to the long axis of the screw component or helical in shape), circular fenestrated holes that follow the flute trajectory, or a combination of both.

The sleeve component is characterized by a body having external male bone screw threading with a pitch that can be equal to, smaller than, or greater than the thread pitch of the screw component, an internal bore extending from a proximal end of the sleeve component to the distal end of the sleeve component and sized for reception over the proximal end of the screw component, and internal female machine screw threading with a geometry configured to mate with the external male machine screw threading of the screw component.

The bone compression screw may be used in the following manners in order to provide compression of a bone joint or bone fracture (boney anatomy). One manner is to install the screw component to a desired depth into the boney anatomy, then independently drive the sleeve component about the screw component while the screw component remains fixed. Another manner is to install the screw component and the sleeve component as one component to a desired depth into the boney anatomy, then independently drive either the screw component or the sleeve component further into the boney anatomy.

In one form, the bone compression screw may have two or more expandable segments that are driven outwardly via the sleeve component or via an internal drive shaft of the screw component. The expandable segments may also be driven outwardly perpendicular to the long (longitudinal) axis of the screw component or outwardly at a forward angle with respect to the long axis of the screw component. Moreover, the outer surface of the expandable segments can be either smooth (no surface texture) or with any variation of surface texture including, but not limited to, tooth geometry, knurled geometry, horizontal grooved geometry, or vertical grooved geometry.

In this form, the bone compression screw provides compression of a bone joint or bone fracture while also expanding within the boney anatomy. The purpose of the expandable segments is to provide resistance to rotational forces and hence rotation of the bone compression screw while in the boney anatomy. This may be accomplished in several manners. One manner is to install the bone compression screw as an assembled component to a desired depth in the boney anatomy, then independently drive the sleeve component about the screw component while the screw component remains fixed, whereby the sleeve screw component performs the expansion of the segments. Another manner is to install the bone compression screw as an assembled component to a desired depth in the boney anatomy, then independently drive an inner drive shaft about the long axis of the screw component in order to perform expansion of the segments.

In one form, the bone compression screw may have two or more tangs that are configured to flare outwardly as the bone compression screw is installed. The purpose of the tangs is to provide resistance to rotational forces and hence rotation of the bone compression screw while in the boney anatomy. The tangs are incorporated into the sleeve component and are forced outwardly as the sleeve screw component is driven downward about the screw component. The tangs may formed in different sizes to provide various arc lengths.

In this form, the bone compression screw provides compression of a bone joint or bone fracture while also affording a secondary means of boney fixation in order to provide resistance to rotational forces. This can be accomplished by installing the bone compression screw as an assembled component to a desired depth, then independently driving the sleeve component about the screw component while the screw component remains fixed, whereby the tangs of the sleeve component are driven into the bone.

Further aspects of the present invention will become apparent from consideration of the drawings and the following description of embodiments of the invention. A person skilled in the art will realize that other embodiments of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate forms of the present invention, wherein.

DETAILED DESCRIPTION OF THE INVENTION

Figure 1:
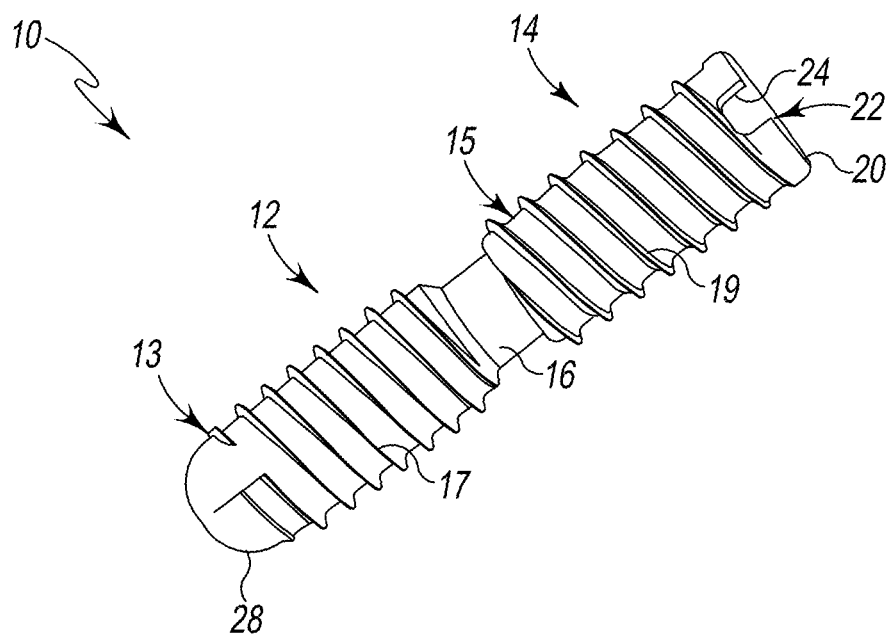
FIG. 1 is a side view of an exemplary form of a bone compression screw fashioned in accordance with the principles of the present invention.
Figure 2:
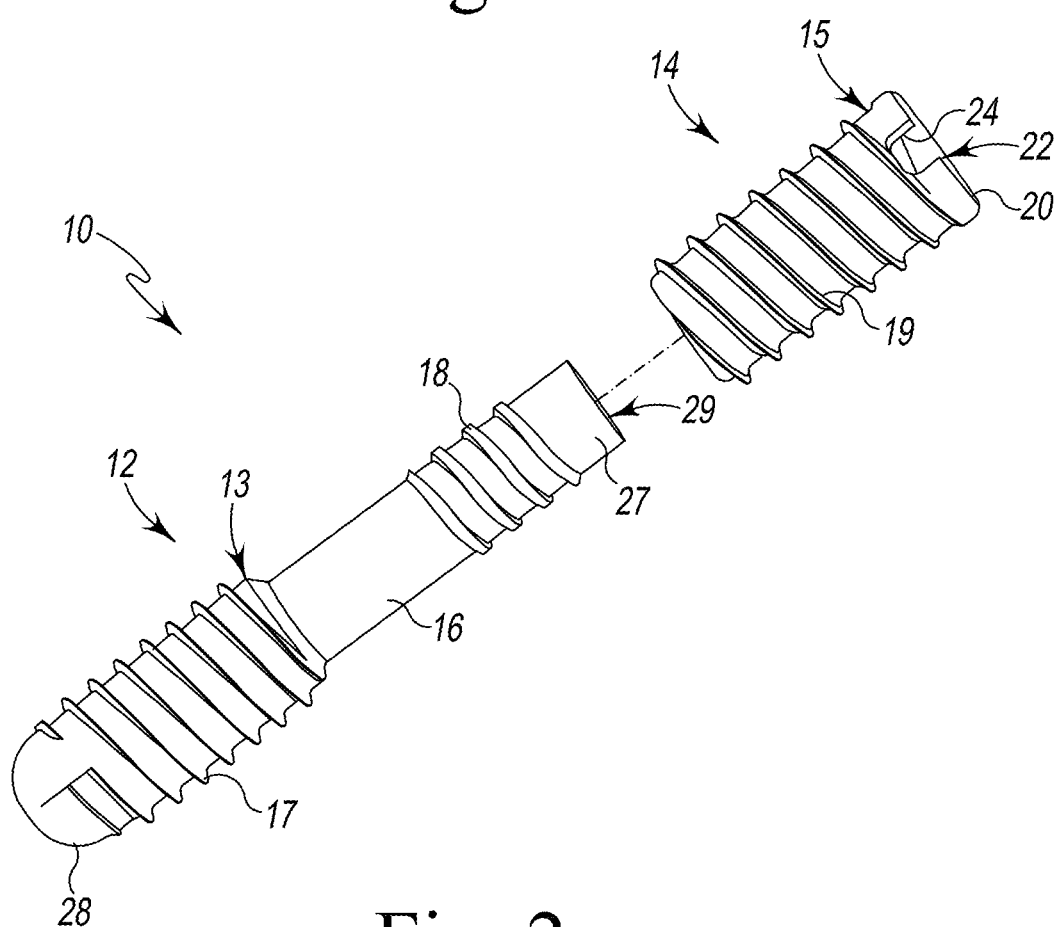
FIG. 2 is an exploded view of the bone compression screw of FIG. 1.

Referring to FIGS. 1 and 2, there is depicted an exemplary form of a bone compression screw, generally designated 10, for compressing two bone or boney anatomies such as, but not limited to, a bone joint or bone fracture. The bone compression screw 10 comprises a screw component 12 and a sleeve component 14. The screw component 12 and the sleeve component 14 are fashioned from a known biocompatible implant material.

The screw component 12 is characterized by a body 13 having a distal end 28 with external male bone screw threads or threading 17, a smooth shank 16, and a proximal end 27 with external male machine screw threads or threading 18. In this form, the body 13 is solid except for a configured socket 29 at the proximal end 27. The configured socket 29 may be hexagonal shaped to receive a hexagonal driving tool (not shown) such as is known in the art. Of course, other configurations may be used.

Figure 6:
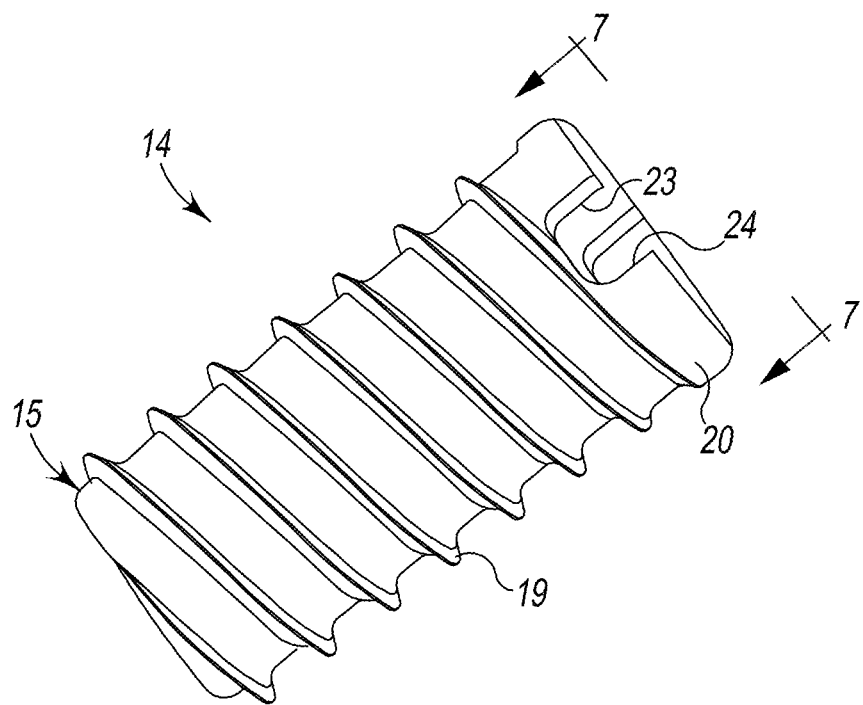
FIG. 6 is an enlarged view of the sleeve component of the bone compression screws of FIGS. 1-5.
Figure 7:
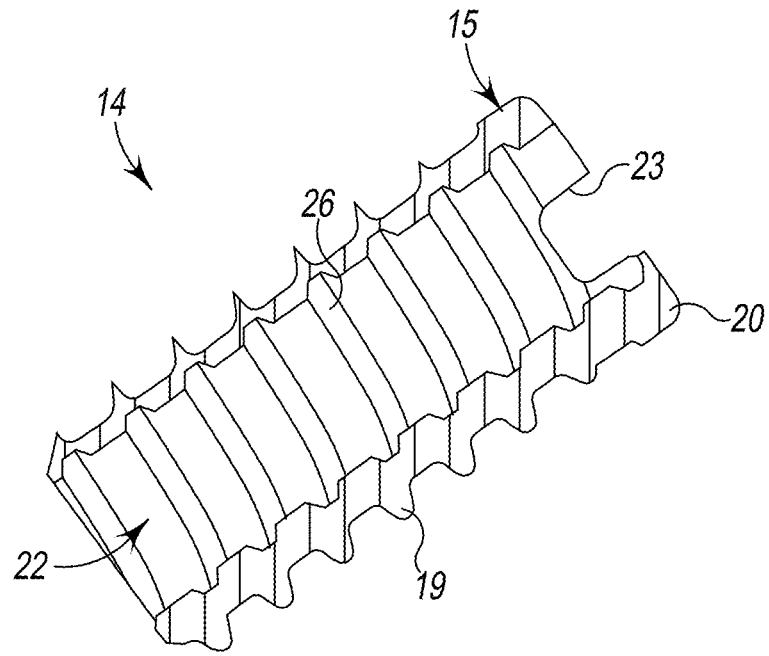
FIG. 7 is an enlarged sectional view of the sleeve component of FIG. 6 taken along line 7-7 thereof.

With additional reference to FIGS. 6 and 7, the sleeve component 14 is characterized by a body 15 having external male bone screw threads or threading 19 with a thread pitch that is equal to, smaller than, or larger than the thread pitch of the external male bone screw threads 17 of the screw component 12. The body 15 further has a bore 22 that extends the length of the body 15 and is sized to be received over and onto the proximal end 27 of the screw component 12. The body 15 further has internal female machine screw threads or threading 26 in the bore 22 that are/is configured to mate with the external male machine screw threads/threading 18 of the proximal end 27 of the screw component 12. The body 15 further has a head 20 with two notches 23, 24. The two notches 23, 24 are disposed in the head 20 opposite one another and allow a driving tool to engage and independently drive the sleeve component 14 relative to the screw component 12. While two notches 23, 24 are shown, the head 20 may have more than two notches if desired.

Figure 3:
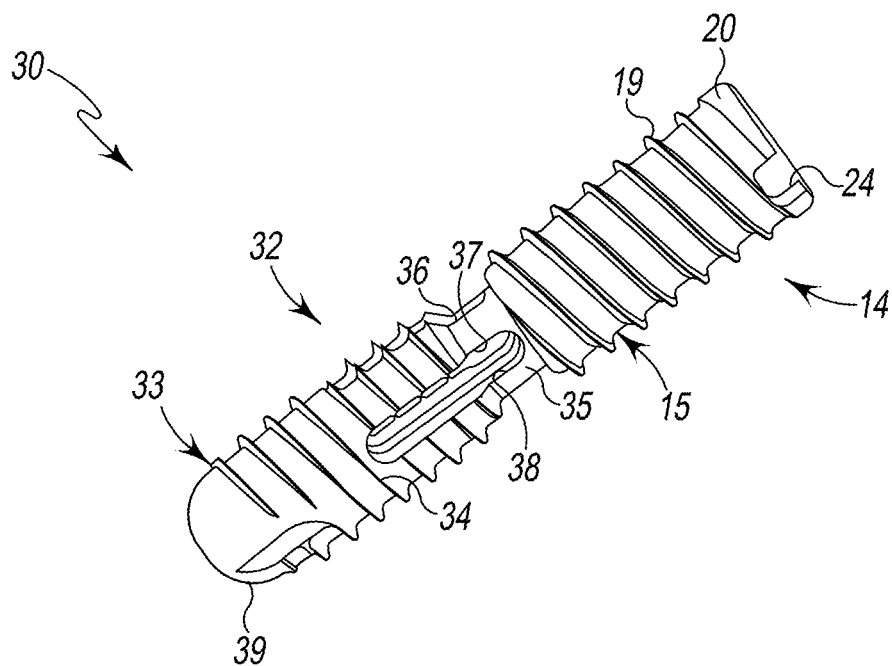
FIG. 3 is a side view of an exemplary form of a slotted and cannulated bone compression screw fashioned in accordance with the principles of the present invention.

Referring to FIG. 3, there is shown another exemplary form of a bone compression screw, generally designated 30, for compressing two bone or boney anatomies such as, but not limited to, a bone joint or bone fracture. The bone compression screw 30 comprises a screw component 32 and the sleeve component 14 as described above with respect to the bone compression screw 10 and, as such, will not be described again with respect to the bone compression screw 30. The screw component 32 is fashioned from a known biocompatible implant material.

The screw component 32 is characterized by a body 33 having a distal end 39 with external male bone screw threads or threading 34, a smooth shank 35, and a proximal end (not shown, but the same as the proximal end 27 of the screw component 12) with external male machine screw threads or threading (not shown, but the same as the external male machine screw threads 18 of the screw component 12). In this form, the body 33 is generally solid except for a configured socket (not shown, but the same as the configured socket 29 of the screw component 12) at the proximal end of the body 33, and four (4) slots or openings 36, 37, 38, and another not seen in FIG. 3. The configured socket of the body 33 may be hexagonal shaped to receive a hexagonal driving tool (not shown) such as is known in the art. Of course, other configurations may be used. Each one of the four slots 36, 37, 38, and the one not seen in FIG. 3, extend from the smooth shank 35 of the body 33 to and through the external male bone screw threads/threading 34 of the distal end 39 of the body 33. While the four slots are evenly spaced about the body 33, other configurations may be used, additionally, more or less slots may be used.

Figure 4:
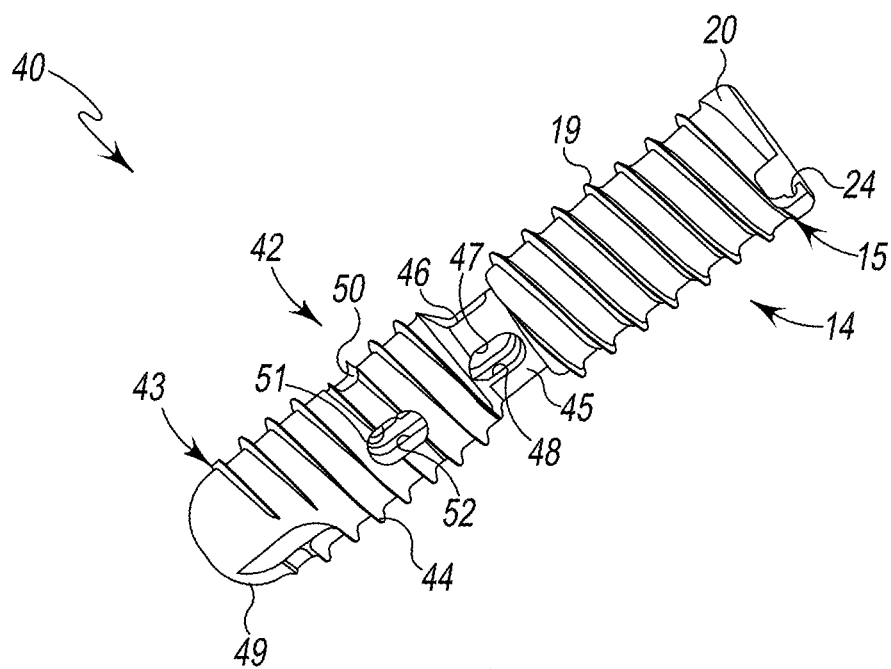
FIG. 4 is a side view of an exemplary form of a fenestrated and cannulated bone compression screw fashioned in accordance with the principles of the present invention.

Referring to FIG. 4, there is shown another exemplary form of a bone compression screw, generally designated 40, for compressing two bone or boney anatomies such as, but not limited to, a bone joint or bone fracture. The bone compression screw 40 comprises a screw component 42 and the sleeve component 14 as described above with respect to the bone compression screw 10 and, as such, will not be described again with respect to the bone compression screw 40. The screw component 42 is fashioned from a known biocompatible implant material.

The screw component 42 is characterized by a body 43 having a distal end 49 with external male bone screw threads or threading 44, a smooth shank 45, and a proximal end (not shown, but the same as the proximal end 27 of the screw component 12) with external male machine screw threads or threading (not shown, but the same as the external male machine screw threads 18 of the screw component 12). In this form, the body 43 is generally solid except for a configured socket (not shown, but the same as the configured socket 29 of the screw component 12) at the proximal end of the body 33, and two sets of four (4) fenestrae or openings 46, 47, 48, and another not seen in FIG. 4 constituting a first set, and 50, 51, 52, and another not seen in FIG. 4 constituting a second set, the nomenclature first and second being arbitrary. The configured socket of the body 43 may be hexagonal shaped to receive a hexagonal driving tool (not shown) such as is known in the art. Of course, other configurations may be used. Each one of the first set of four fenestrae 46, 47, 48, and the one not seen in FIG. 4, are situated in the smooth shank 45 of the body 43. Each one of the second set of four fenestrae 50, 51, 52 and the one not seen in FIG. 4 are situated in the distal end 49 and the external male bone screw threads/threading 44 of the body 33. While all of the fenestrae are evenly spaced about the body 43, other configurations may be used. Additionally, more or less fenestrae may be used.

Figure 5:
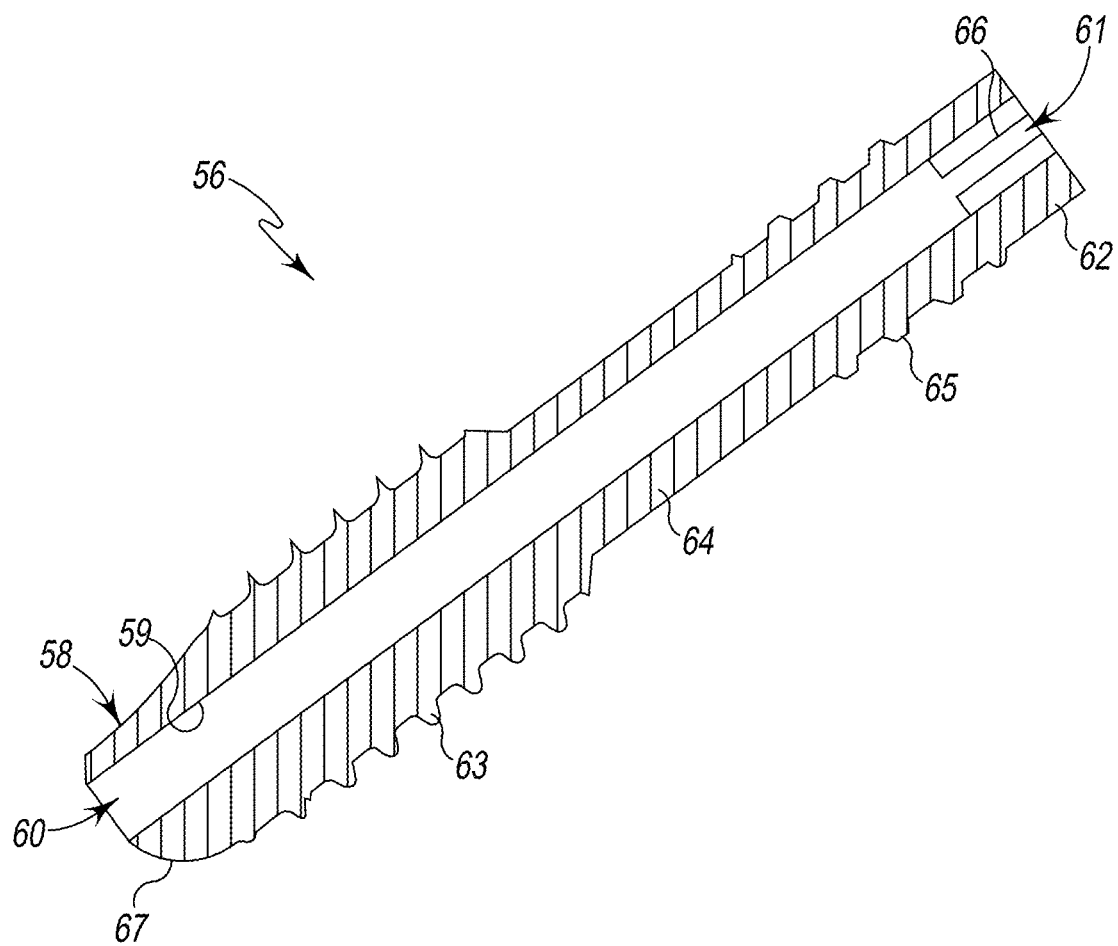
FIG. 5 is a sectional view of an exemplary form of a cannulated screw component for a bone compression screw as shown herein.

Referring to FIG. 5, there is shown a sectional view of an exemplary form of a screw component, generally designated 56. The screw component 56 is characterized by a body 58 having a distal end 67 with external male bone screw threads or threading 63, a smooth shank 64, and a proximal end 62 with external male machine screw threads or threading 65. The body 58 is cannulated and thus has a longitudinal bore 59 having an opening 60 at the distal end 67 of the body 58, and an opening 61 in the proximal end 62 of the body 58. The body 58 further has a configured socket 66 at the proximal end 62. The configured socket 66 may be hexagonal shaped to receive a hexagonal driving tool (not shown) such as is known in the art. Of course, other configurations may be used. The screw component 56 illustrates that a screw component may be cannulated rather than being solid. The screw component 42 is fashioned from a known biocompatible implant material. The sleeve component 14 as described above with respect to the bone compression screw 10 is used with the screw component 56 and, as such, will not be described again.

The bone compression screws 10, 30, 40 and their permutations, provide compression of boney anatomies. Without being exhaustive, this may be accomplished in a couple of manners. One manner is to install the screw component into the boney anatomies requiring compression, install the sleeve component onto the screw component, then independently drive the sleeve component about the screw component while the screw component remains fixed until the boney anatomies are joined as desired. Another manner is to install the screw component and the sleeve component as one device to a desired depth in the boney anatomies, then independently drive either the screw component and the sleeve component further into the boney anatomies until the boney anatomies are joined as desired.

Referring now to FIGS. 8-14, there is shown another exemplary form of a bone compression screw, generally designated 70, for compressing two bone or boney anatomies such as, but not limited to, a bone joint or bone fracture. The bone compression screw 70 comprises a screw component 72 and the sleeve component 14 as described above with respect to the bone compression screw 10 and, as such, will not be described again with respect to the bone compression screw 70. The screw component 72 is fashioned from a known biocompatible implant material.

The screw component 72 is characterized by a body 73 having a distal end 79 with external male bone screw threads or threading 74, a smooth shank 75, and a proximal end 90 with external male machine screw threads or threading 88. The body 73 is cannulated and thus has a longitudinal bore 84 having an opening 85 at the distal end 79 of the body 73, and an opening 86 in the proximal end 90 of the body 73. The body 73 further has a configured socket 87 at the proximal end 90. The configured socket 87 may be hexagonal shaped to receive a hexagonal driving tool (not shown) such as is known in the art. Of course, other configurations may be used. The body 73 further has three (3) fenestrae or openings 78, 82, 89 each one of which is situated in the smooth shank 75. In accordance with this form of bone compression screw, an expandable segment 77, 80, 83 is respectively positioned in each fenestrae 78, 82, 89—i.e. expandable segment 77 is positioned in fenestra 78, expandable segment 80 is positioned in fenestra 82, and expandable segment 83 is positioned in fenestra 83. Each expandable segment 76, 80, 83 is generally triangular in sectional with a generally curved outer surface to generally match the curvature of the smooth shank 75 of the screw component 72. While three (3) fenestrae and three (3) expandable segments are shown, the bone compression screw 70 can have at least two (2) fenestrae and two (2) corresponding expandable segments or more than three (3) fenestrae and three (3) expandable segments.

The outer surface of each expandable segment 76, 80, 83 is shown having longitudinal (vertical) grooves/grooved geometry. However, the outer surface of each expandable segment may have no texture (smooth), a tooth/toothed geometry, a knurled geometry, horizontal groove geometry, other texture geometry/texturing, or a combination of these geometries. Additionally, each expandable segment 76, 80, 83 has a respective fenestra or opening 77, 81, and one not seen in the figures for segment 83, that provide communication with the respective fenestra 78, 82, 89 of the body 73 in which the expandable segment is situated. Each expandable segment 76, 80, 83 is movable with respect to the body 73. Particularly, each expandable segment 76, 80, 83 is movable outwardly (expanded) with respect to the body 73 by way of the secondary screw component 14 (as depicted in the figures) or by way of an internal drive shaft (not shown). More particularly, each expandable segment 76, 80, 83 is driven outwardly perpendicular to the long (longitudinal) axis of the primary screw component 72 (as shown) or may be driven outwardly at a forward angle with respect to the long axis of the primary screw component 72.

Figure 8:
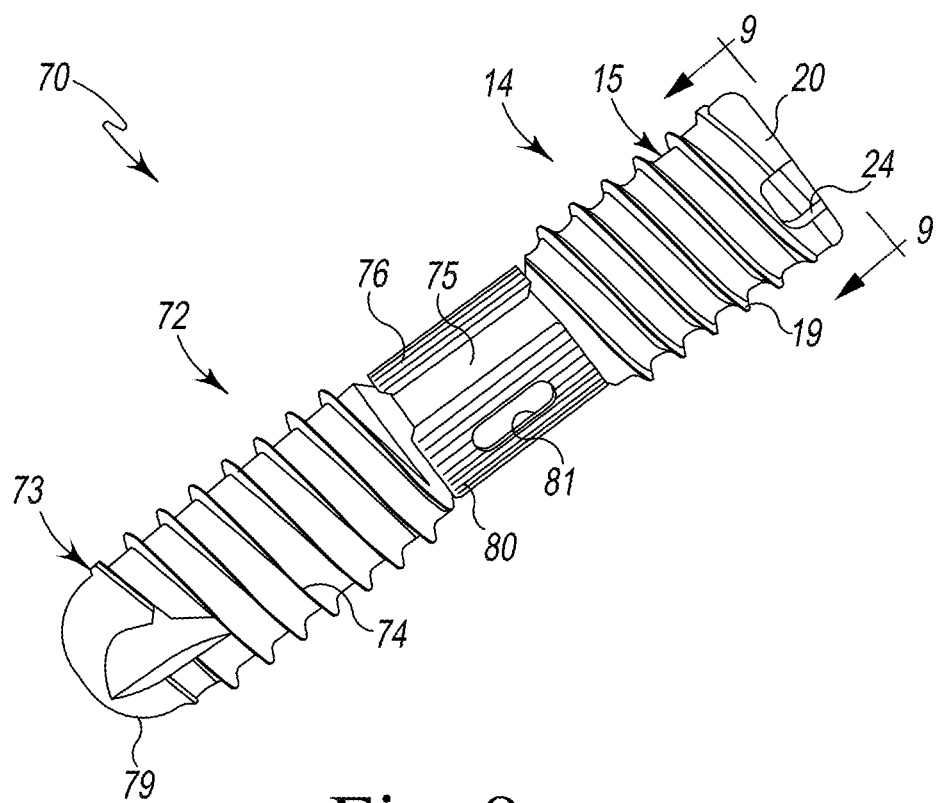
FIG. 8 is a side view of an exemplary form of a fenestrated and cannulated bone compression screw incorporating expandable segments fashioned in accordance with the principles of the present invention, the expandable segments shown unexpanded.
Figure 9:
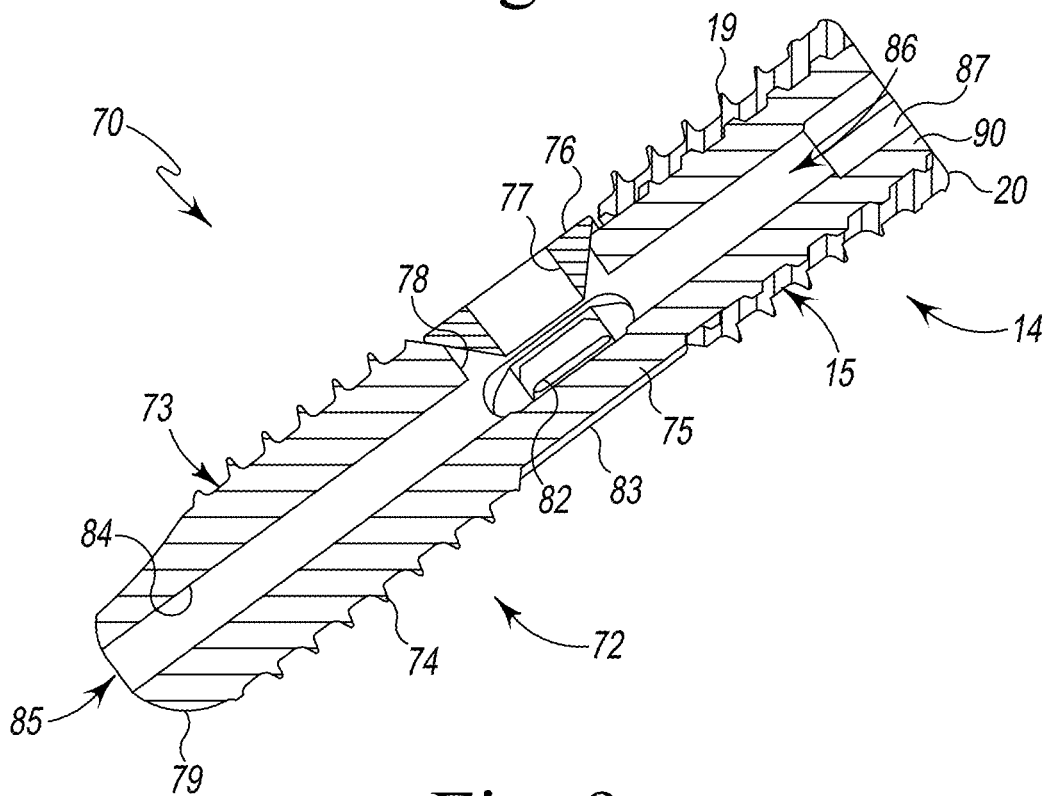
FIG. 9 is a sectional view of the fenestrated and cannulated bone compression screw with expandable segments of FIG. 8 taken along line 9-9 thereof.
Figure 10:
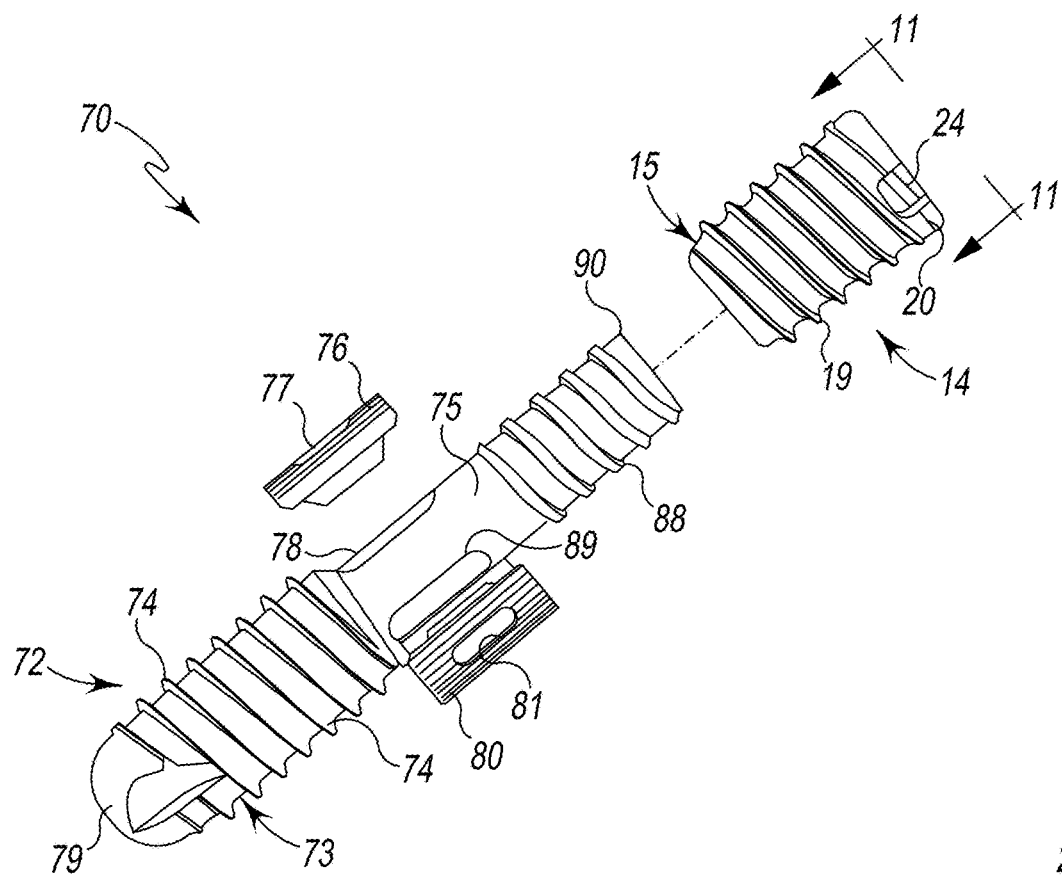
FIG. 10 is an exploded view of the fenestrated and cannulated bone compression screw with expandable segments of FIG. 8.
Figure 11:
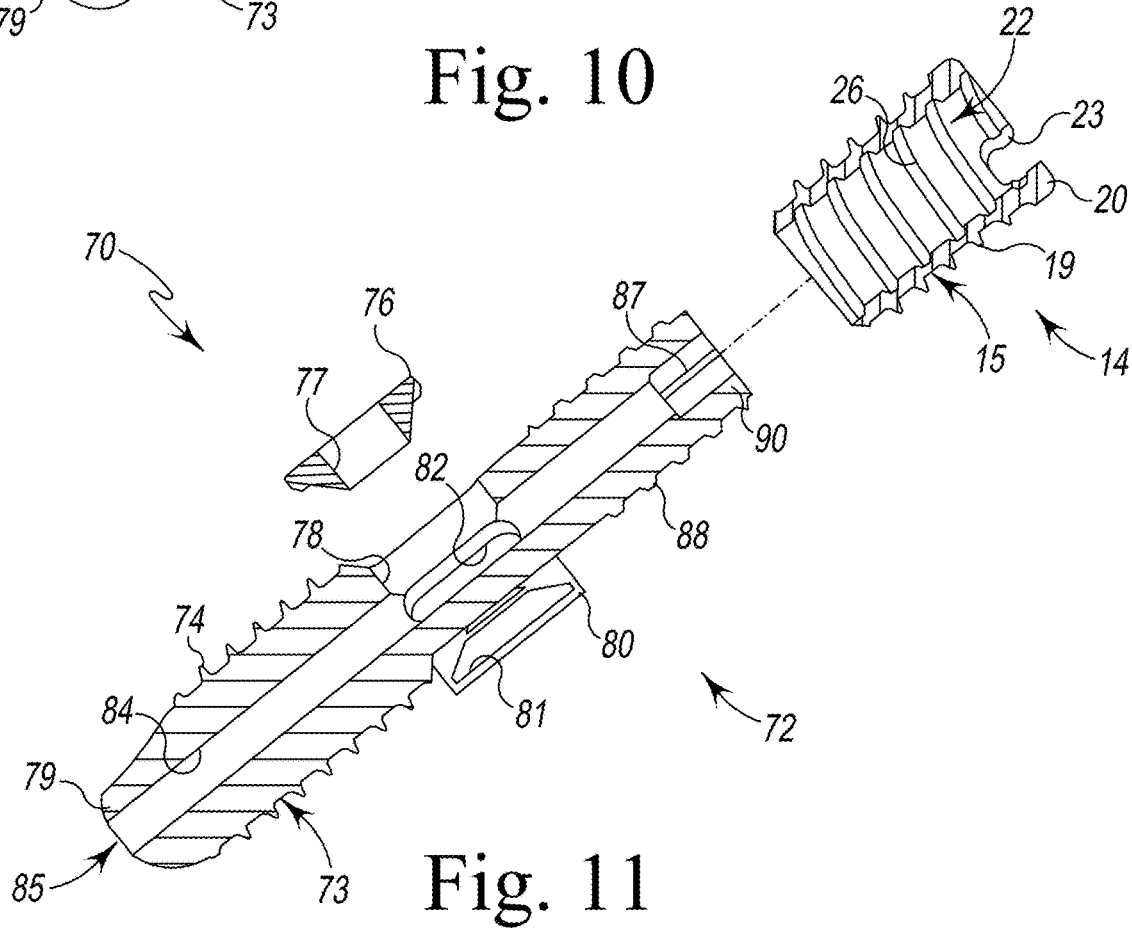
FIG. 11 is an exploded sectional view of the fenestrated and cannulated bone compression screw with expandable segments of FIG. 10 taken along line 11-11 thereof.
Figure 12:
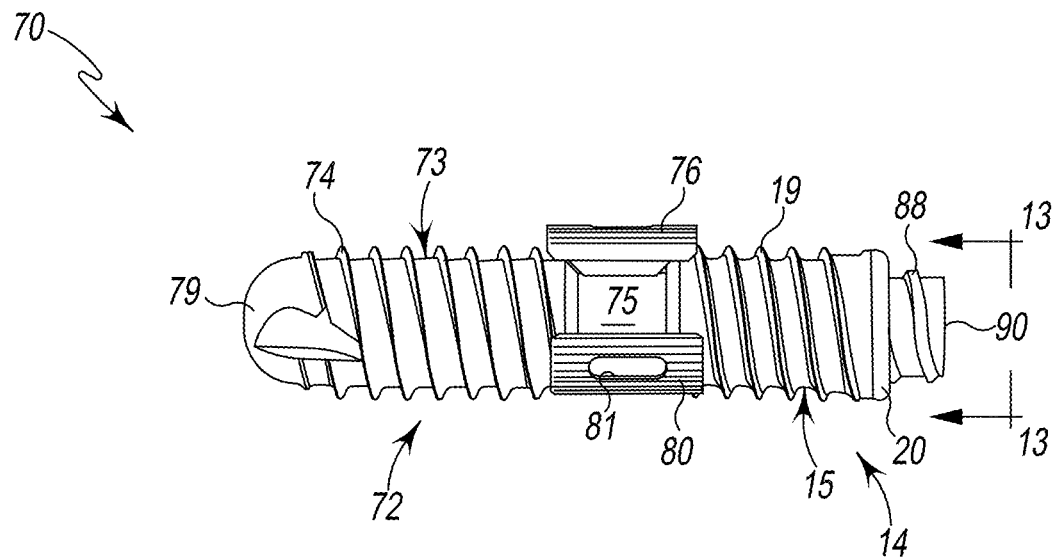
FIG. 12 is a side view of the fenestrated and cannulated bone compression screw with expandable segments of FIG. 8 with the expandable segments shown in an expanded position by rotation of the secondary screw component relative to the primary screw component thereof.
Figure 13:
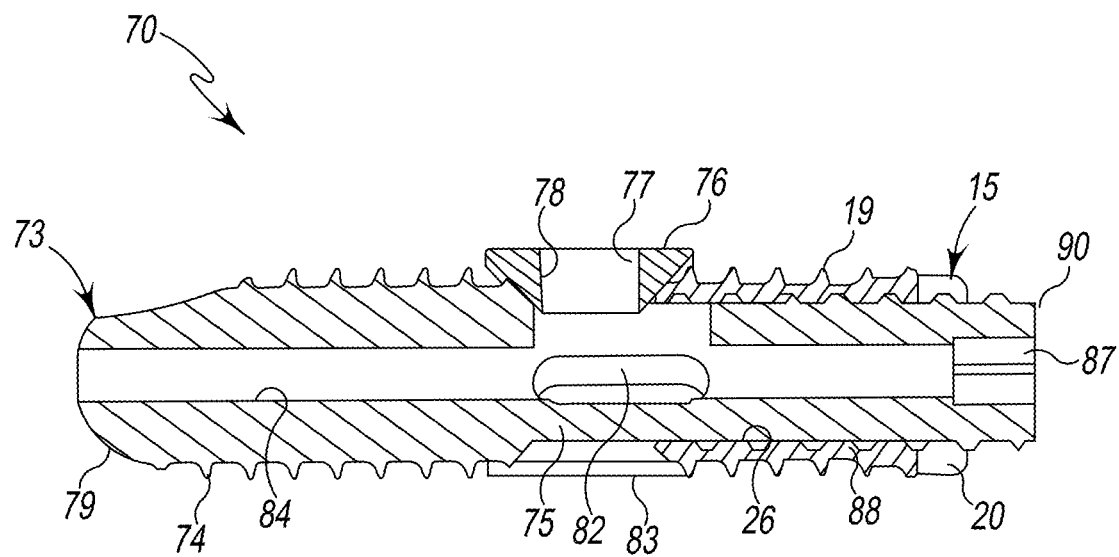
FIG. 13 is a sectional view of the fenestrated and cannulated bone compression screw with expanded segments of FIG. 12 taken along line 13-13 thereof.
Figure 14:
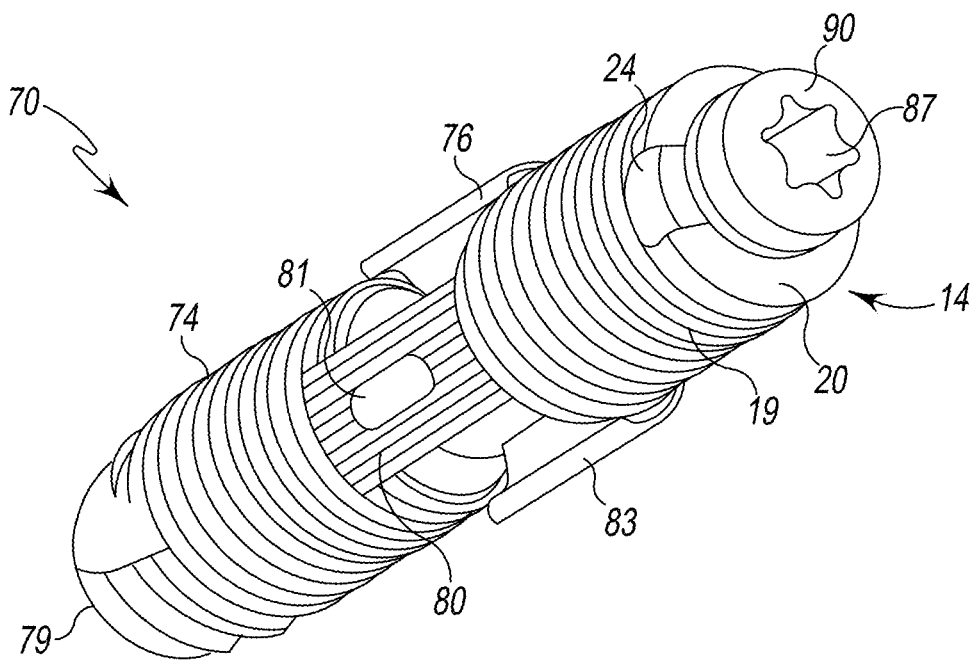
FIG. 14 is a top isometric view of the fenestrated and cannulated bone compression screw with expandable segments of FIG. 8 with the expandable segments in an expanded position through rotation of the sleeve component relative to the screw component.

FIGS. 8 and 9 depict the bone compression screw 70 in an unexpanded state (i.e. wherein the expandable segments 76, 80, 83 have not been driven outwardly by the secondary screw component 14), while FIGS. 12-14 depict the bone compression screw 70 in an expanded state (i.e. wherein the expandable segments 76, 80, 83 have been driven outwardly by the sleeve component 14). In the unexpanded state, the angled sides of each expandable segment is resting against the sides of the respective fenestra of the screw component body (see FIG. 9). When the sleeve component 14 is driven relative to the screw component, the end of the sleeve component pushes against the near angled side of each expandable segment to push or drive the expandable segment outward (see FIG. 13). The expandable segments are thus driven or expand into the boney anatomy to provide resistance to rotational forces.

The bone compression screw 70 provides compression of boney anatomies. Without being exhaustive, this may be accomplished in a couple of manners. One manner is to install the bone compression screw 70 as an assembled component to a desired depth into the boney anatomies, then independently drive the sleeve component 14 about the screw component 72 while the screw component 72 remains fixed, whereby the sleeve component 14 performs the expansion of the segments 76, 80, 83. Another manner is to install the bone compression screw 70 as an assembled component to a desired depth into the boney anatomies, then independently drive an inner drive shaft about the long axis of the screw component in order to perform expansion of the segments—it being appreciated that this embodiment is not shown in the figures.

Referring to FIGS. 15-22 there is shown another exemplary form of a bone compression screw, generally designated 100, for compressing two bone or boney anatomies such as, but not limited to, a bone joint or bone fracture. The bone compression screw 100 comprises a screw component 102 and a form of the sleeve component 14 as described above with respect to the bone compression screw 10, generally designated 104. The screw component 102 and the sleeve component 104 are fashioned from a known biocompatible implant material.

The screw component 102 is characterized by a body 103 having a distal end 118 with external male bone screw threads or threading 107, a smooth shank 106, and a proximal end 119 with external male machine screw threads or threading 108. The body 103 is cannulated and thus has a longitudinal bore 125 having an opening 124 at the distal end 118 of the body 103, and an opening 126 in the proximal end 119 of the body 103. The body 103 further has a configured socket 127 at the proximal end 119. The configured socket 127 may be hexagonal shaped to receive a hexagonal driving tool (not shown) such as is known in the art. Of course, other configurations may be used. The body 103 further has four (4) slots or openings 115, 116, 117 each one of which is situated in and extends from the smooth shank 106 to the threaded distal end of the body 103. While four (4) slots are shown, the bone compression screw 100 can have at least two (2) slots.

Figure 17:
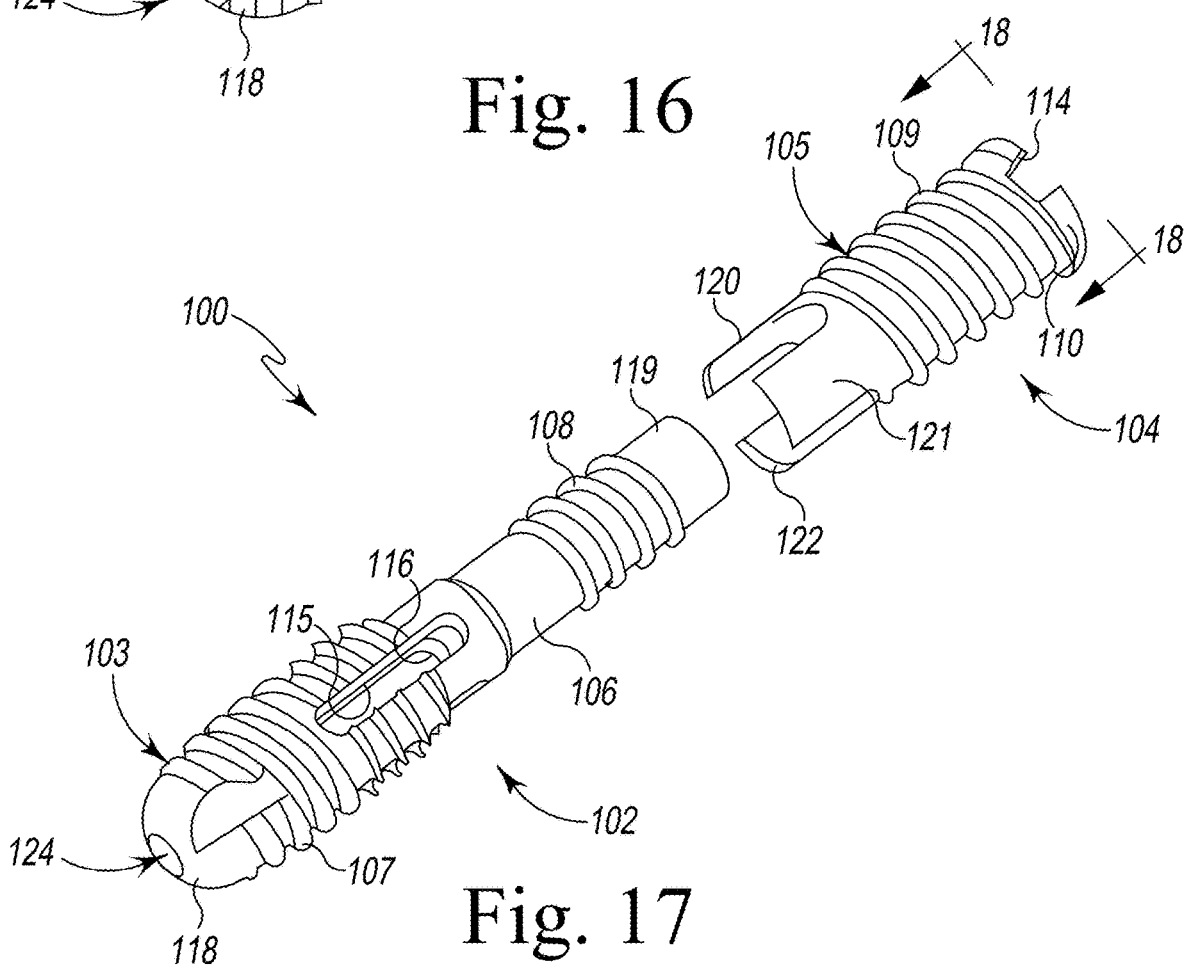
FIG. 17 is an exploded view of the slotted and cannulated bone compression screw with expandable tangs of FIG. 15.
Figure 18:
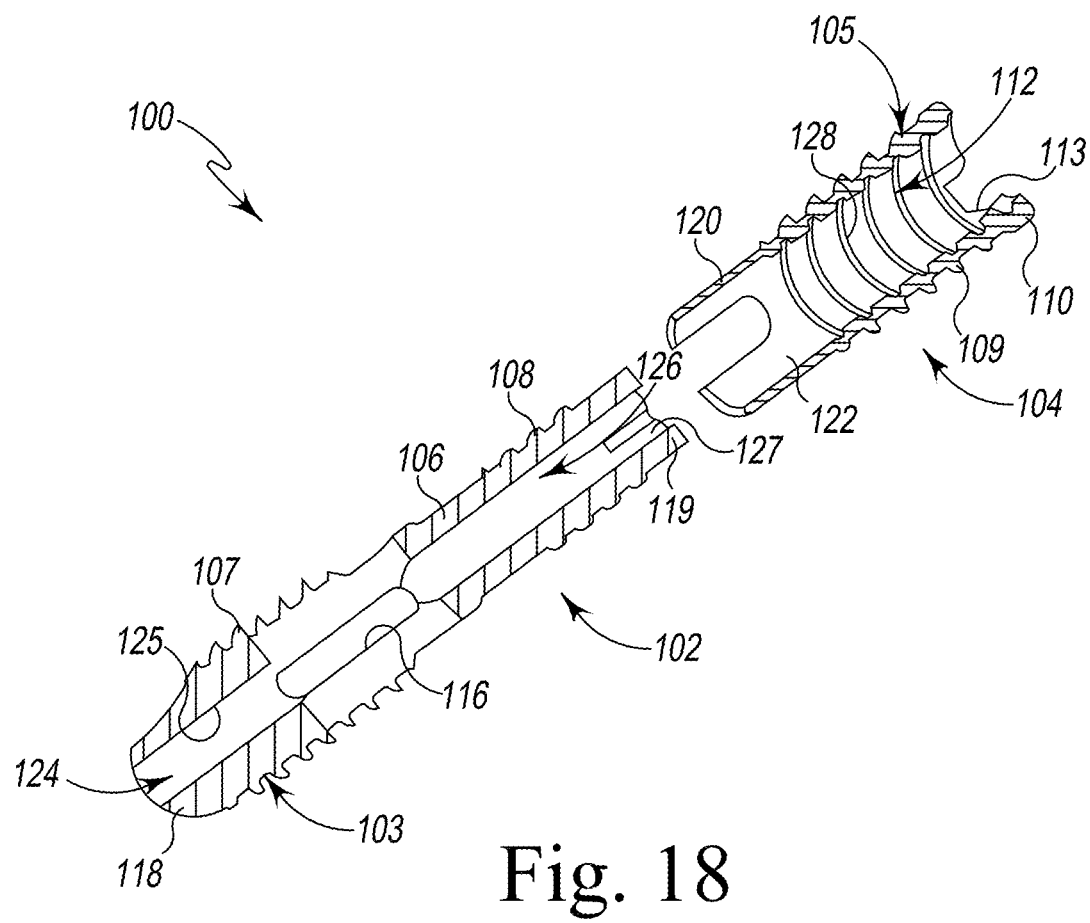
FIG. 18 is an exploded sectional view of the slotted and cannulated bone compression screw with expandable tangs of FIG. 17 taken along line 18-18 thereof.

With particular reference to FIGS. 17 and 18, the sleeve component 104 is characterized by a body 105 having external male bone screw threads or threading 109 with a thread pitch that is equal to, smaller than, or larger than the thread pitch of the external male bone screw threads 108 of the screw component 102. The body 105 further has a bore 112 that extends the length of the body 105 and is sized to be received over and onto the proximal end 127 of the screw component 102. The body 105 further has internal female machine screw threads or threading 128 in the bore 112 that are/is configured to mate with the external male machine screw threads/threading 108 of the proximal end 127 of the screw component 102. The body 105 further has a head 110 with two notches 113, 114. The two notches 113, 114 are disposed in the head 110 opposite one another and allow a driving tool to engage and independently drive the sleeve component 104 relative to the screw component 102. While two notches 113, 114 are shown, the head 110 may have more than two notches if desired.

In accordance with this form of a bone compression screw, the sleeve component 104 has three (3) tangs 120, 121, 122 that extend from a distal end of the body 105. The length and width of the tangs 120, 121, 122 are preferably, but not necessarily, all the same. Additionally, while three (3) tangs are shown, the sleeve component can have two (2) tangs at various arc lengths, or more than three (3) tangs and may be configured in such a way that the openings correspond in number and/or shape to the slots/fenestrations of the primary screw component. Longitudinal length of the tangs may also vary than what is depicted. In use, the tangs 120, 121, 122 are flared (i.e. forced outwardly) as the sleeve component 104 is driven downwardly about the screw component 102. This provides an anti-rotation feature to the bone compression screw 100.

Figure 15:
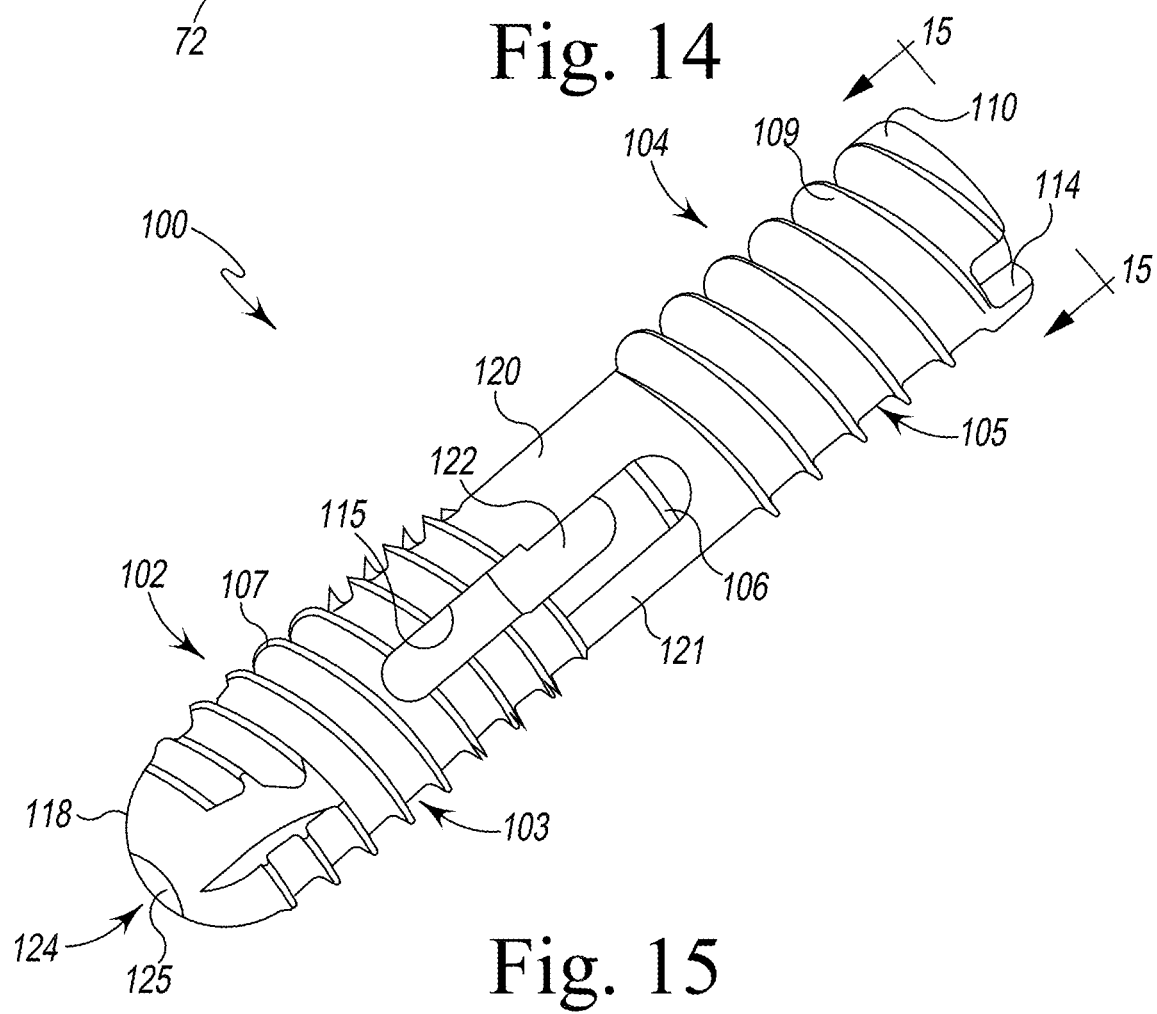
FIG. 15 is a side view of an exemplary form of a slotted and cannulated bone compression screw incorporating expandable tangs fashioned in accordance with the principles of the present invention, the expandable tangs shown unexpanded.
Figure 16:
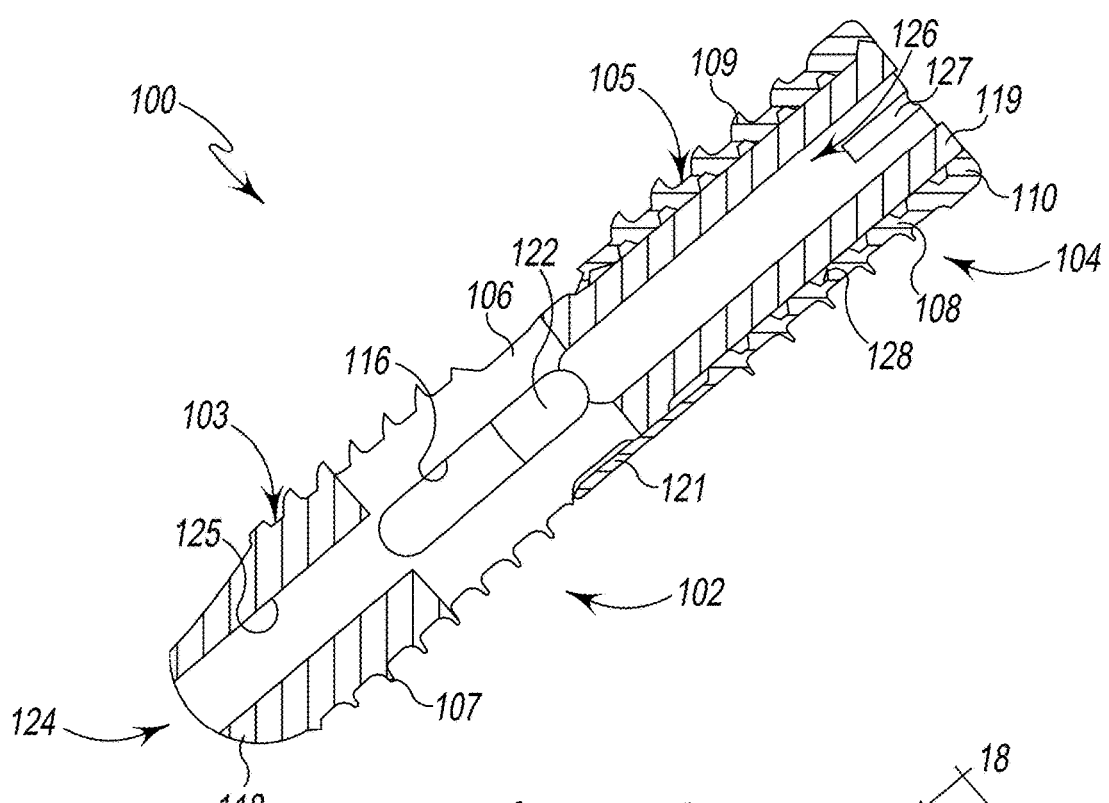
FIG. 16 is a sectional view of the slotted and cannulated bone compression screw with expandable tangs of FIG. 15 taken along line 16-16 thereof.
Figure 19:
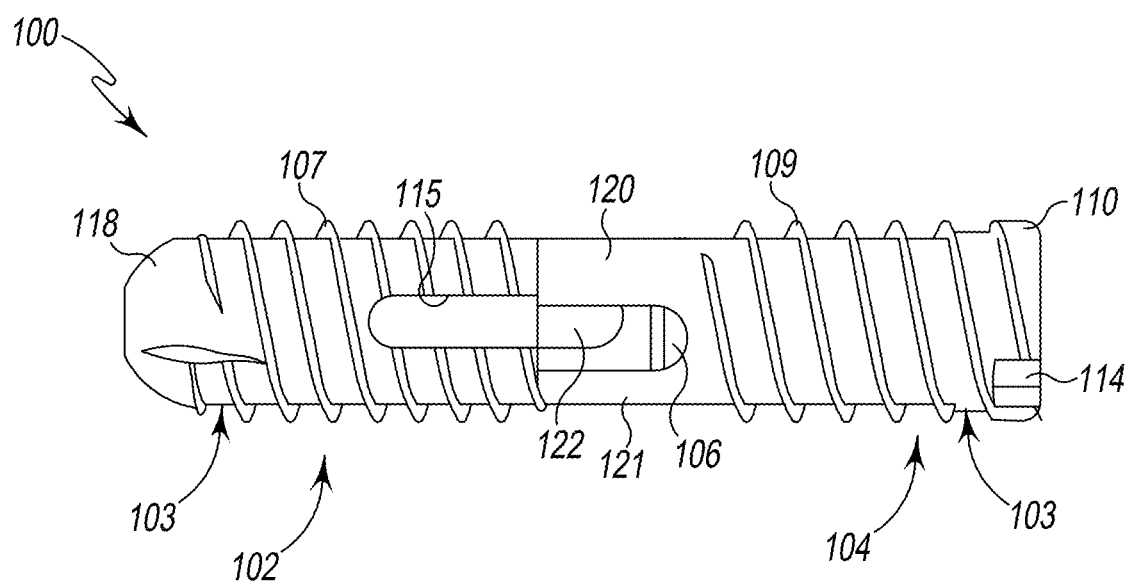
FIG. 19 is a side view of the slotted and cannulated bone compression screw with expandable tangs of FIG. 15.
Figure 20:
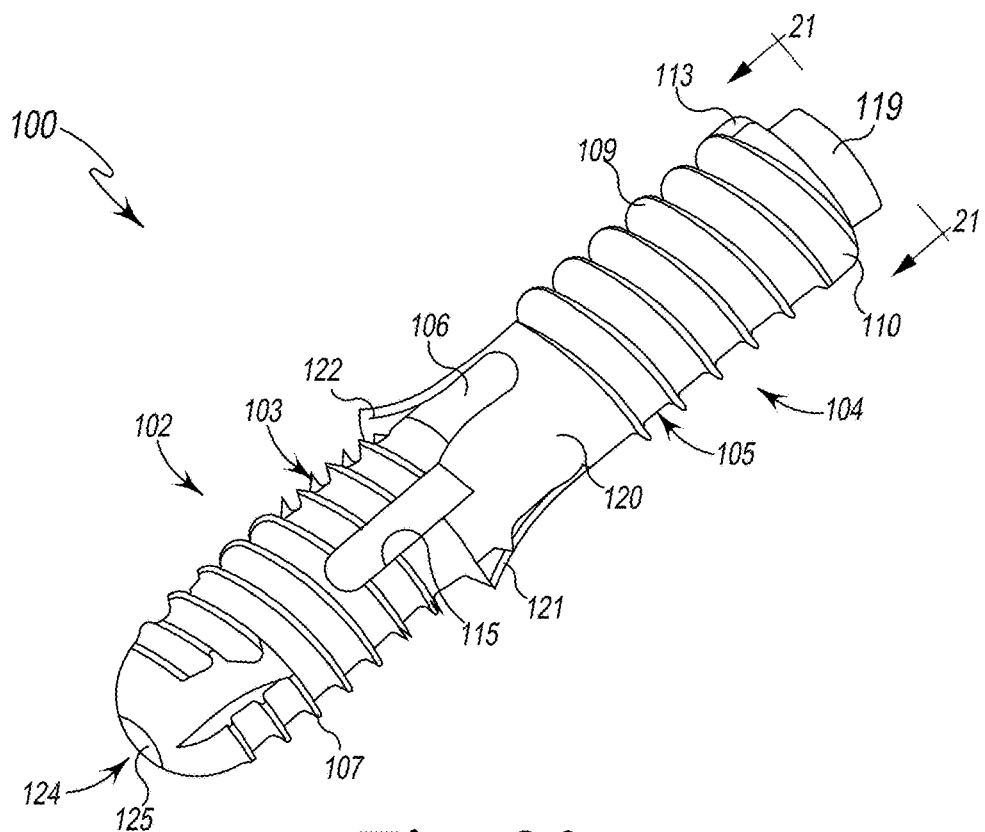
FIG. 20 is a side view of the slotted and cannulated bone compression screw with expandable tangs of FIG. 15, with the expandable tangs in an expanded position by rotation of the sleeve component relative to the screw component.
Figure 21:
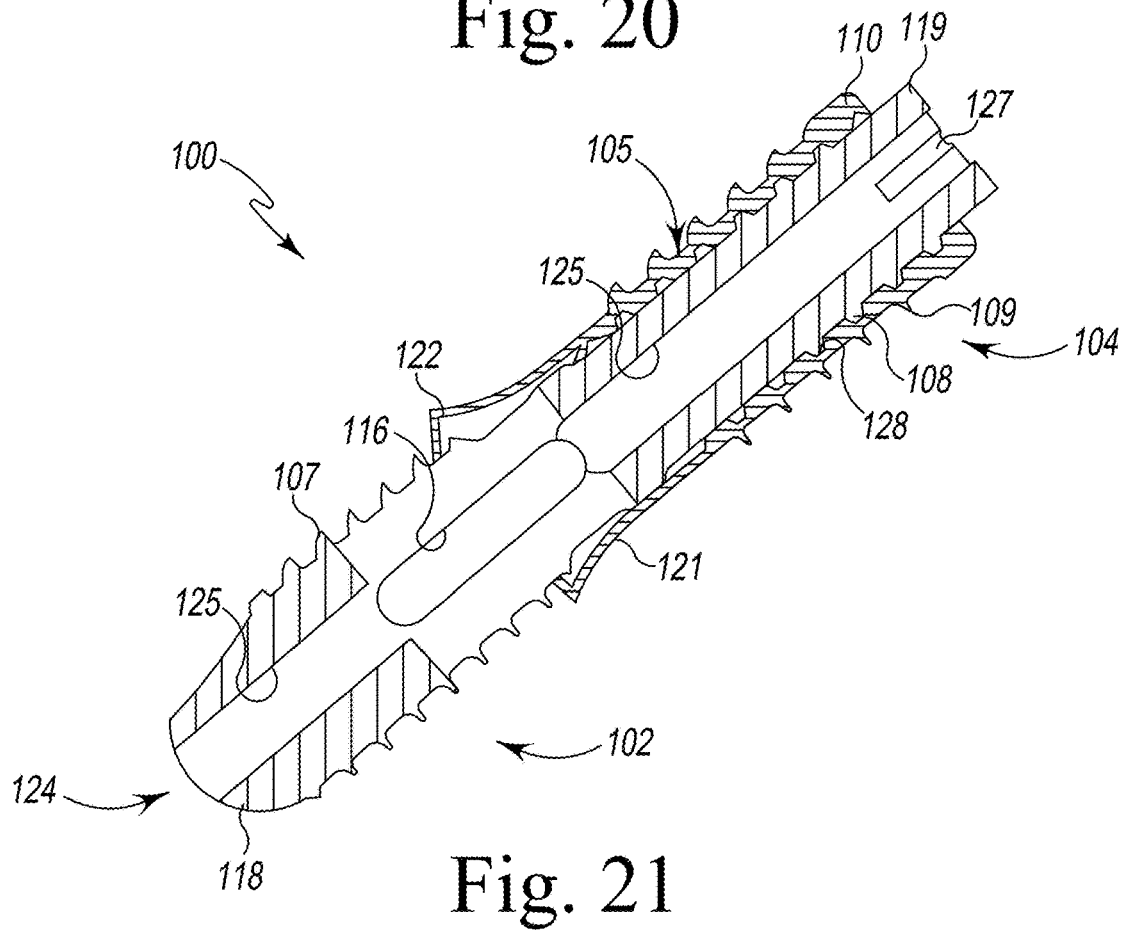
FIG. 21 is a sectional view of the slotted and cannulated bone compression screw with expanded expandable tangs of FIG. 20 taken along line 21-21 thereof.
Figure 22:
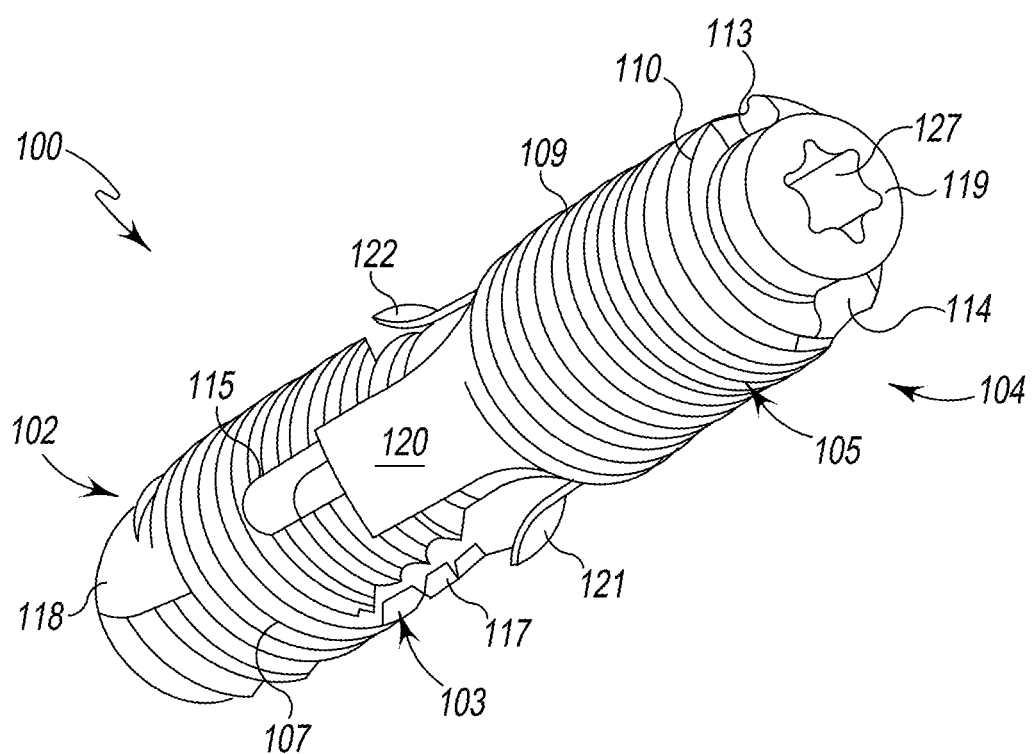
FIG. 22 is a top isometric view of the slotted and cannulated bone compression screw with expandable tangs of FIG. 15 with the expandable segments in an expanded position by rotation of the sleeve component relative to the screw component.

FIGS. 15 and 19 depict the bone compression screw 100 in an un-flared state (i.e. wherein the tangs 120, 121, 122 have not been driven outwardly by the sleeve component 14), while FIGS. 20-22 depict the bone compression screw 100 in a flared state (i.e. wherein the tangs 120, 121, 122 have been driven outwardly by the sleeve component 14). In the un-flared state, the tangs 120, 121, 122 extend generally co-axial with the longitudinal axis of the screw component 102. When the sleeve component 104 is driven relative to the screw component, the tangs of the sleeve component are flared outwardly by the bone screw external male bone screw threads of the screw component (see FIGS. 20, 21). The tangs are thus driven or expand into the boney anatomy to provide resistance to rotational forces.

The bone compression screw 100 provides compression of boney anatomies while also affording a secondary means of boney fixation through resistance to rotational forces. Without being exhaustive, this may be accomplished by installing the bone compression screw 100 as an assembled unit to a desired depth in the boney anatomies, then independently driving the sleeve component relative to the screw component while the screw component remains fixed, whereby the tangs of the sleeve component are driven into the boney anatomy.

FIGS. 23-26 illustrates a bone compression screw 140, fashioned in accordance with the present principles, compressing two boney anatomies 200, 300 again, in accordance with the present principles. The bone compression screw 140 comprises a screw component 142 and the sleeve component 14, as described above with respect to the bone compression screw 10 and, as such, will not be described again with respect to the bone compression screw 140. The screw component 142 is fashioned from a known biocompatible implant material.

The screw component 142 is characterized by a body 143 having a distal end 144 with external male bone screw threads or threading 145, a smooth shank 146, and a proximal end 152 with external male machine screw threads or threading 154. In this form, the body 143 is cannulated and thus has a longitudinal bore 150 having an opening 151 at the distal end 144 of the body 143, and an opening 155 in the proximal end 152 of the body 143. The body 143 further has a configured socket 153 at the proximal end 152. The configured socket 153 may be hexagonal shaped to receive a hexagonal driving tool (not shown) such as is known in the art. Of course, other configurations may be used. The body 73 further has several slots or openings of which two (2) slots 148, 149 are seen in plane with the view and two (2) slots are perpendicular to the view, all of which are situated in and extend between the smooth shank 146 and the bone screw threading 145 of the distal end 144.

Figure 23:
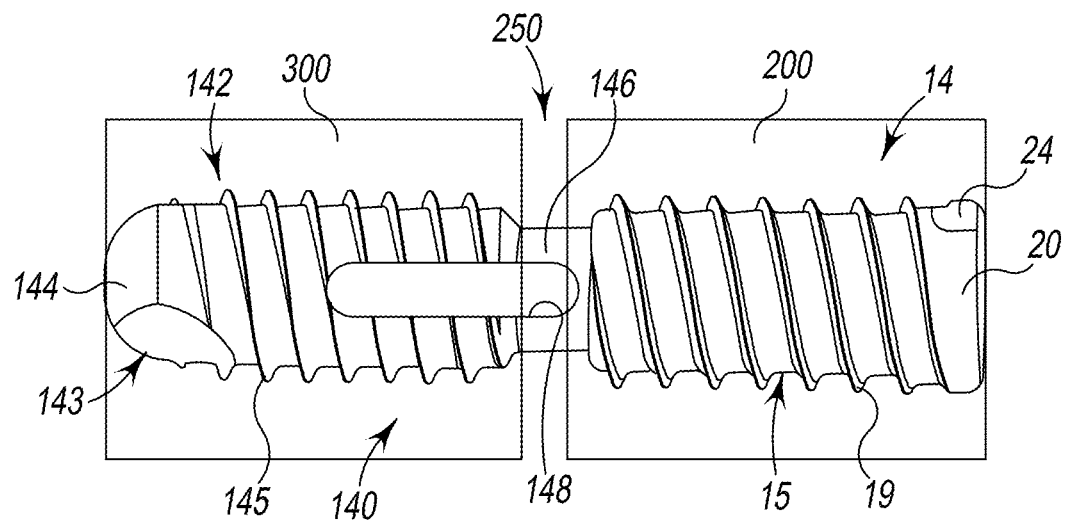
FIG. 23 is a side view of two, separated boney anatomies representing a bone joint, bone fracture, or other boney anatomy with an exemplary form of a slotted and cannulated bone compression screw fashioned in accordance with the present principles that has been initially installed into the two, separated bony anatomies.
Figure 24:
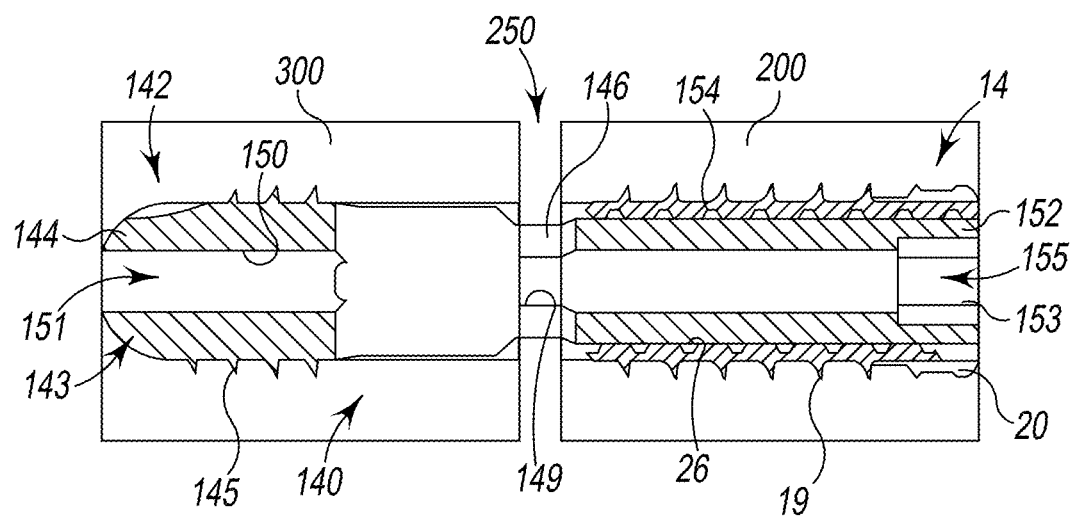
FIG. 24 is a side sectional view of the two, separated boney anatomies with the slotted and cannulated bone compression screw of FIG. 23.
Figure 25:
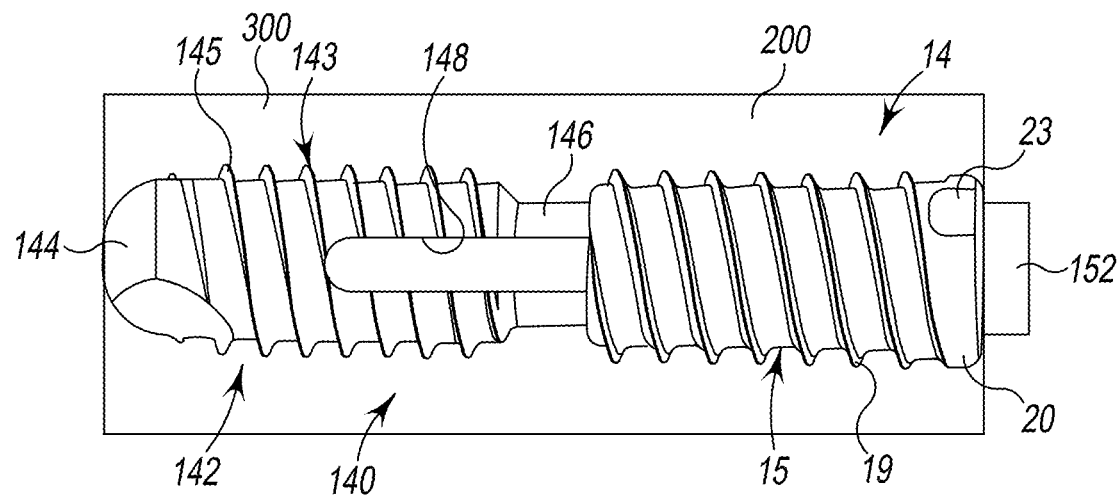
FIG. 25 is a side view of the two boney anatomies of FIGS. 23 and 24 joined together after independently driving the sleeve component about the screw component while the primary screw component remains fixed relative to the sleeve component.
Figure 26:
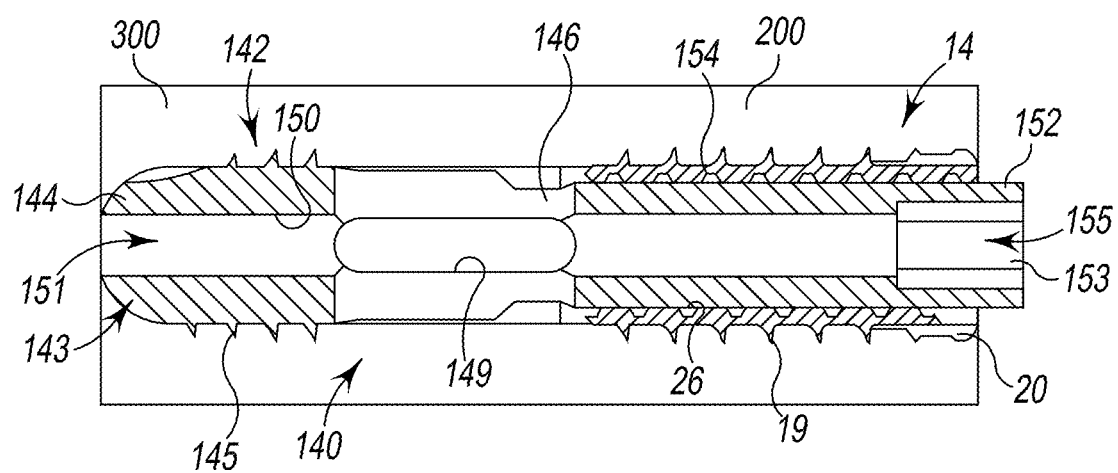
FIG. 26 is a side sectional view of the joined boney anatomies of FIG. 25.
Figure 27:
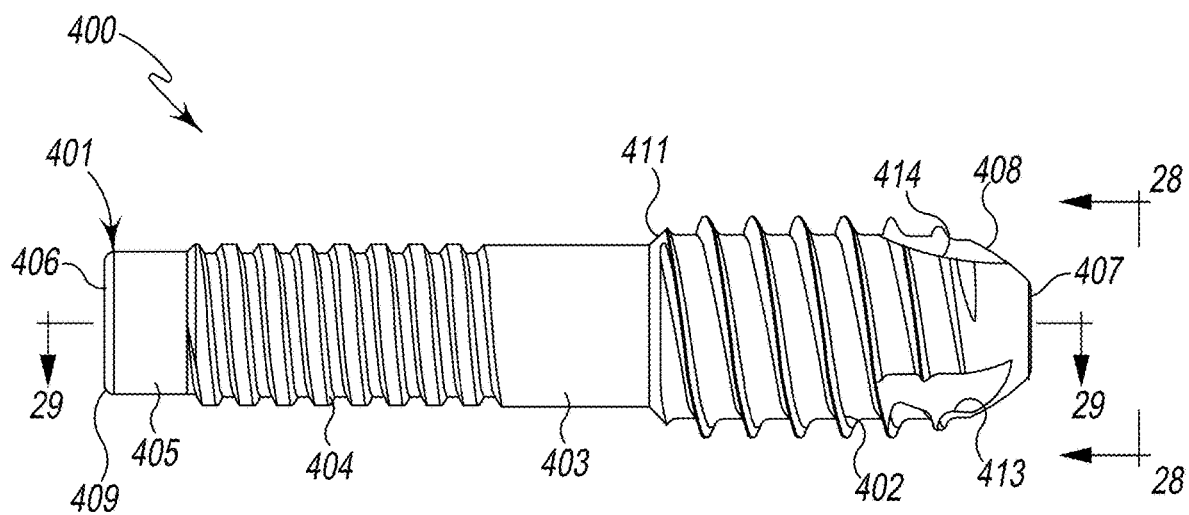
FIG. 27 is a side view of another exemplary form of a cannulated screw component for a bone compression screw fashioned in accordance with the principles of the present invention.

The bone compression screw 140 operates and installs in the same manner as the bone compression screws 10, 30, 40 and their permutations described above and thus will not be re-described. FIGS. 23 and 24 show the bone compression screw 140 having been installed into the boney anatomies 200, 300 as one unit in order to compress the two boney anatomies 200, 300 together and thus close the gap 250, with FIG. 24 showing a sectional view of the bone compression screw 140. FIGS. 25 and 26 shows the bone compression screw 140 after the sleeve component 14 has been driven independently relative to the screw component 142 while the screw component 142 remained fixed, whereby the two boney anatomies 200, 300 have been compressed together such that there is no longer a gap.

Referring to FIGS. 27-31, there is shown another exemplary form of screw component, generally designated 400, of a bone compression screw for compressing two bone or boney anatomies such as, but not limited to, a bone joint or bone fracture. The screw component 400 may be part of a bone compression screw that uses any one of the various sleeve components described herein. The screw component 400 is fashioned from a known biocompatible implant material.

The screw component 400 is characterized by a body 401 having a distal end 407 with external male bone screw threads or threading 402, a smooth shank 403, and a proximal end 406 with a smooth, generally elongated section 405 and external male machine screw threads or threading 404. The proximal end 406 also includes a peripheral bevel 409. The proximal end 406 and the shank 403 have a first diameter, while the distal end 407 has a second diameter that is greater than the first diameter. As a consequence, the distal threading 402 has a greater diameter than the proximal threading 404. A peripheral angle 411 provides a transition between the proximal and distal ends. The distal end 407 has a peripheral angle 408 that makes the distal end arched or bullet shaped with a flat nose. Additionally, first and second notches or thread features 413, 414 are provided in the threads/threading 402. The first and second thread features 413, 414 provide gripping strength to the screw component 400.

Figure 28:
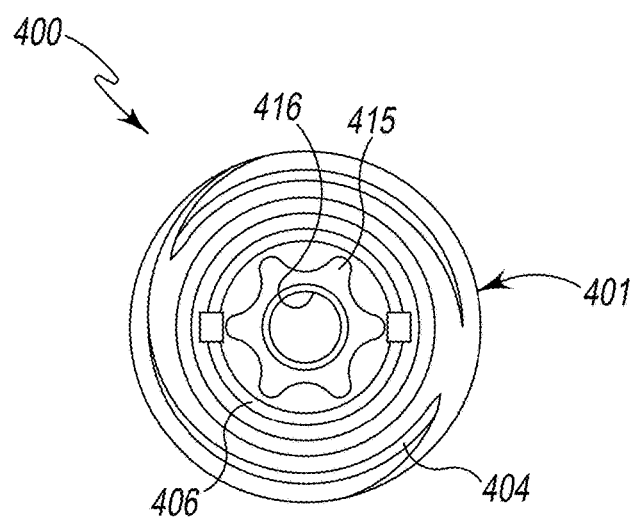
FIG. 28 is an end view of the cannulated screw component of FIG. 27 taken along line 28-28 thereof.
Figure 29:
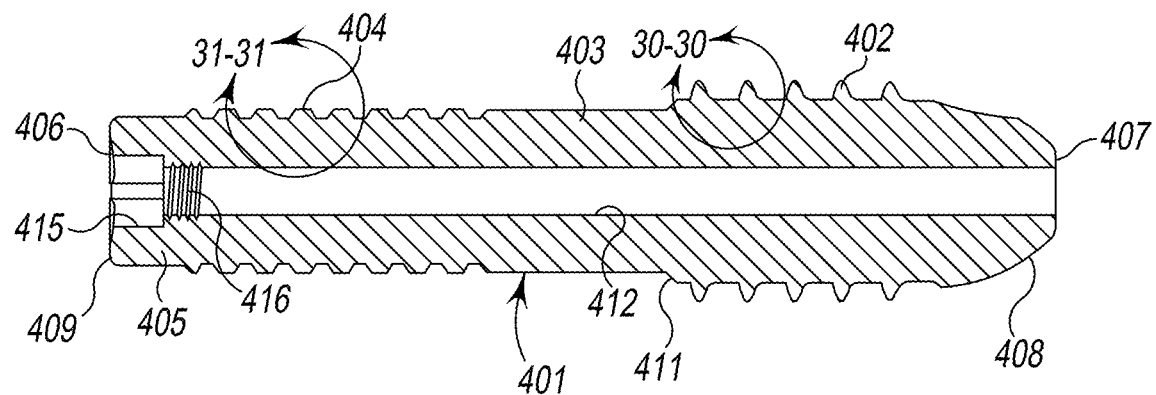
FIG. 29 is a sectional view of the cannulated screw component of FIG. 27 taken along line 29-29 thereof.

In this form, the body 401 is cannulated (has a longitudinal bore) 412 extending through the body 401 from the proximal end 406 to the distal end 407. As seen in FIGS. 28, 29, the proximal end 406 has a configured drive socket 415 at the proximal end opening of the bore 412. The configured drive socket 415 may be hexalobe (hexagonal) shaped to receive a hexalobe driving tool (not shown) such as is known in the art. Of course, other configurations may be used. The bore 412 further includes internal threading 416 axially adjacent to the socket 415, the threading 416 for receiving an installation instrument (not shown).

Figure 30:
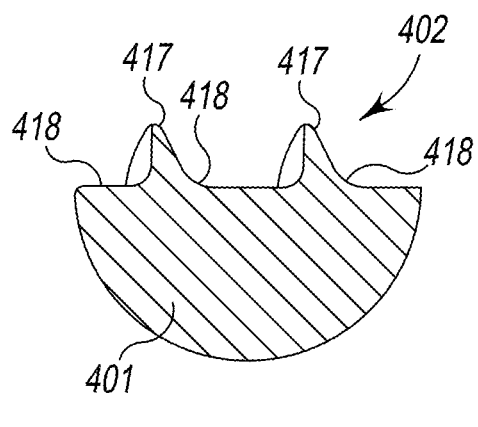
FIG. 30 is an enlarged portion of the cannulated screw component of FIG. 29 taken along circle 30-30 thereof.
Figure 31:
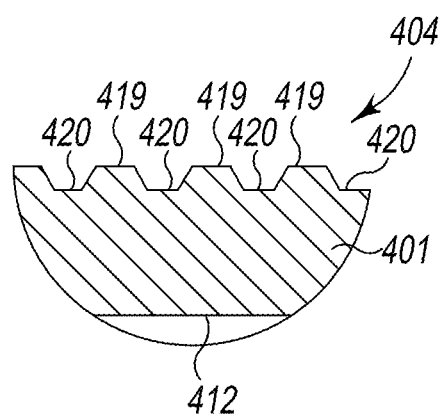
FIG. 31 is an enlarged portion of the cannulated screw component of FIG. 29 taken along circle 31-31 thereof.

FIG. 30 provides an enlarged view of the distal threading 402. The distal threading 402 is characterized by a sharp helical projection 417 winding about the distal end 407. Helical flat 418 is defined between the helical projection 417 and thus likewise forms a spiral path about the distal end. The threading 402 is configured for reception in bone. FIG. 31 provides an enlarged view of the proximal threading 404. The proximal threading 404 is characterized by a flat helical projection 419 winding about the proximal end 406. A helical flat 420 is defined between the helical projection 419 and thus likewise forms a spiral path about the proximal end. The proximal threading 404 is configured to receive the sleeve 430 (see FIGS. 35-41) or the other sleeves described herein.

Figure 32:
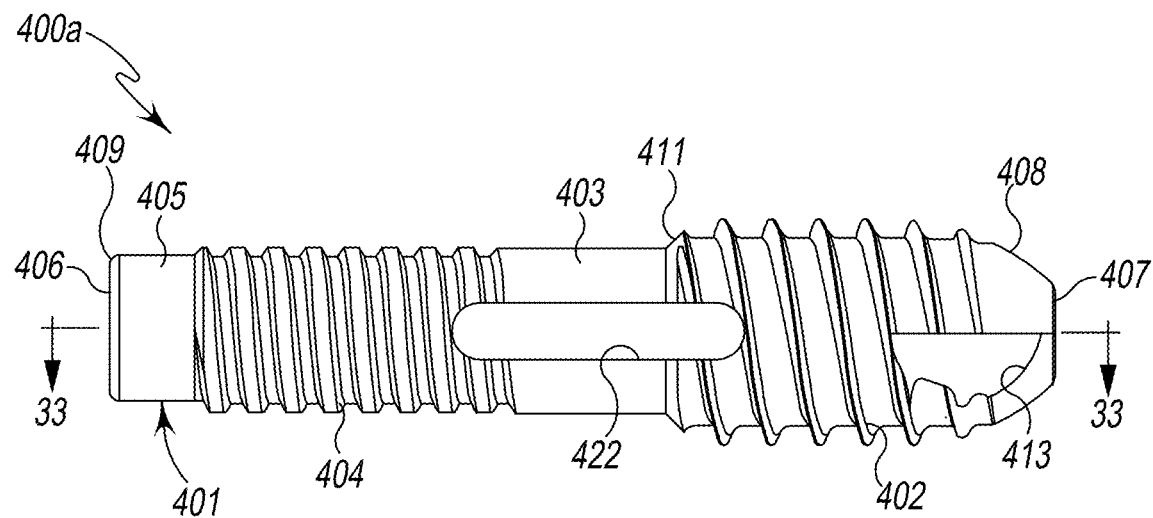
FIG. 32 is a side view of another exemplary form of a cannulated and slotted screw component for a bone compression screw fashioned in accordance with the principles of the present invention.
Figure 33:
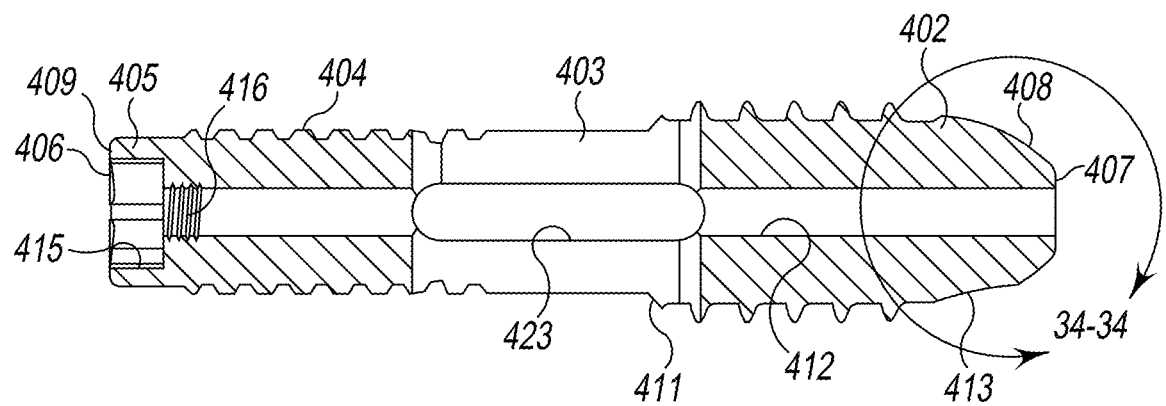
FIG. 33 is a sectional view of the cannulated and slotted screw component of FIG. 32 taken along line 33-33 thereof.
Figure 34:
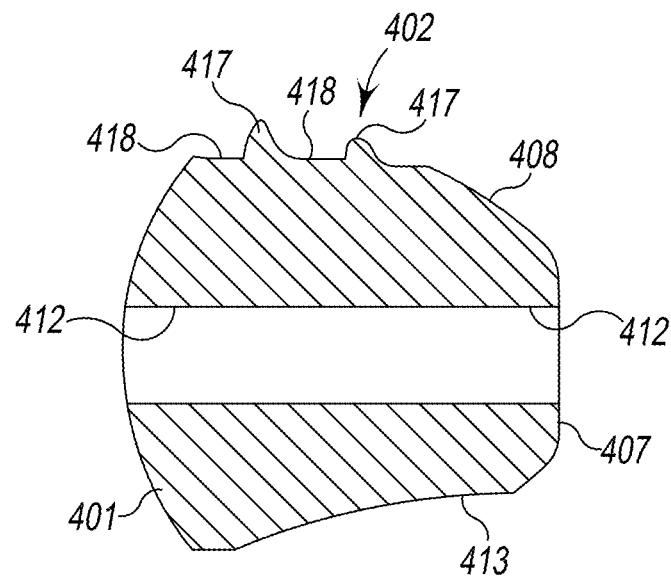
FIG. 34 is an enlarged portion of the cannulated and slotted screw component of FIG. 32 taken along circle 34-34 thereof.
Figure 35:
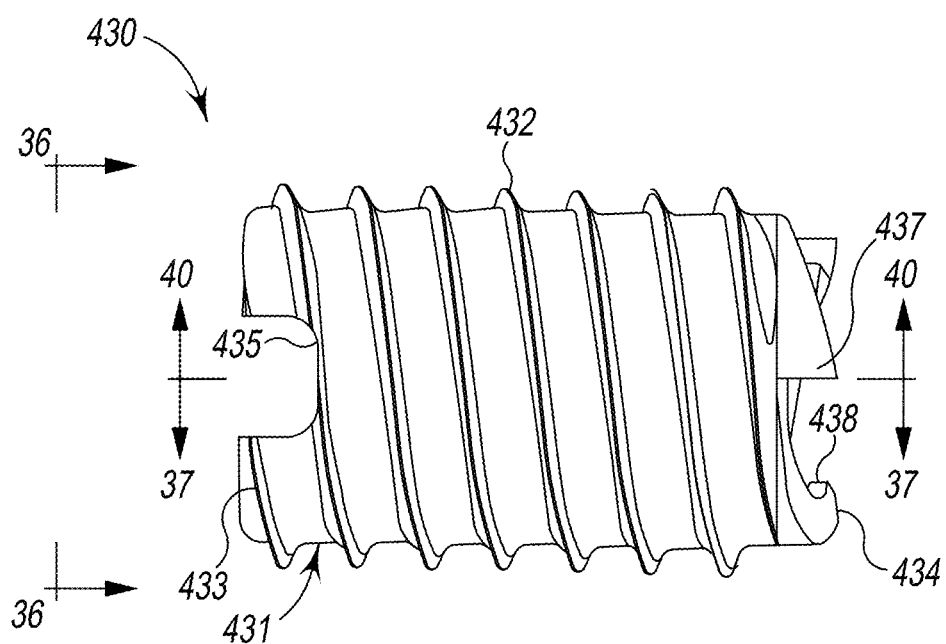
FIG. 35 is a side view of an exemplary form of a sleeve component or sleeve for the bone compression screws of FIGS. 27, 32, 42, 47 and 51.
Figure 36:
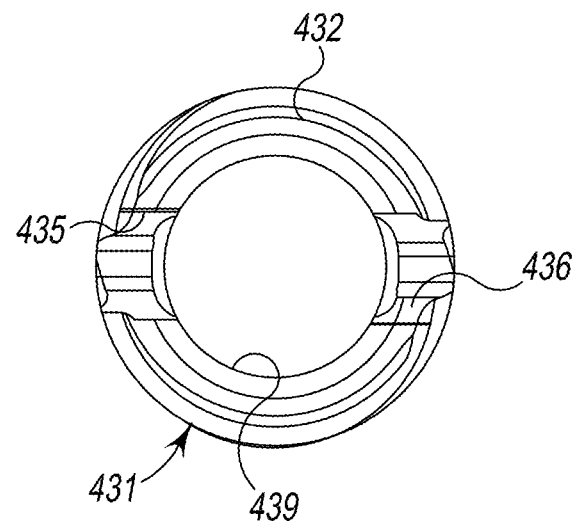
FIG. 36 is an end view of the sleeve screw component of FIG. 35 taken along line 36-36 thereof.
Figure 37:
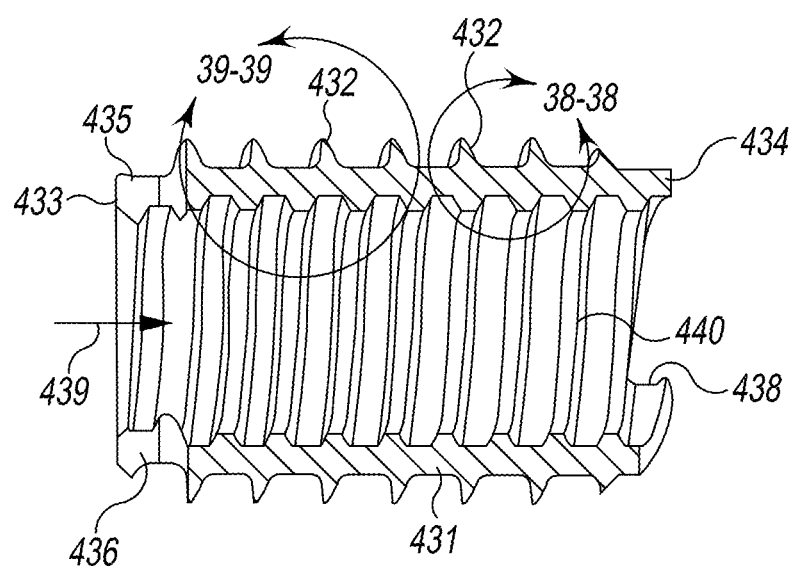
FIG. 37 is a sectional view of the sleeve component of FIG. 35 taken along line 37-37 thereof.

FIGS. 32-34 show another exemplary form of a screw component, generally designated 400a, of a bone compression screw for compressing two bone or boney anatomies such as, but not limited to, a bone joint or bone fracture. The screw component 400a may be part of a bone compression screw that uses any one of the various sleeve components described herein. The screw component 400a is fashioned from a known biocompatible implant material.

The screw component 400a is characterized by a body 401 having a distal end 407 with external male bone screw threads or threading 402, a smooth middle shank 403, and a proximal end 406 with a smooth section 405 and external male machine screw threads or threading 404. The smooth section 405 has a generally elongated length. The proximal end 406 also includes a peripheral bevel 409. The proximal end 406 and the shank 403 have a first diameter, while the distal end 407 has a second diameter that is greater than the first diameter. As a consequence, the distal threading 402 has a greater diameter than the proximal threading 404. A peripheral angle 411 provides a transition between the proximal and distal ends. The distal end 407 has a peripheral angle 408 that makes the distal end arched or bullet shaped with a flat nose. Additionally, first and second notches or thread features 413, 414 are provided in the threads/threading 402. The first and second thread features 413, 414 provide gripping strength to the screw component 400a.

In this form, the body 401 is cannulated (has a longitudinal bore) 412 extending through the body 401 from the proximal end 406 to the distal end 407. As seen in FIG. 33, the proximal end 406 has a configured drive socket 415 at the proximal end opening of the bore 412. The configured drive socket 415 may be hexalobe (hexagonal) shaped to receive a hexalobe driving tool (not shown) such as is known in the art. Of course, other configurations may be used. The bore 412 further includes internal threading 416 axially adjacent to the socket 415, the threading 416 for receiving an installation instrument (not shown).

FIG. 34 provides an enlarged view of the distal threading 402. The distal threading 402 is characterized by a sharp helical projection 417 winding about the distal end 407. Helical flat 418 is defined between the helical projection 417 and thus likewise forms a spiral path about the distal end. The threading 402 is configured for reception in bone. While not shown in detail, the proximal threading 404 is characterized by a flat helical projection winding about the proximal end while a helical flat is defined between the helical projection and thus likewise forms a spiral path about the proximal end. The proximal threading is configured to receive the sleeve 430 (see FIGS. 35-41) or the other sleeves described herein. The screw component 400a further includes four slots of which two slots 422, 423 are seen in FIGS. 32, 33. The four slots are situated at 90° intervals about the body 401. Each slot extends longitudinally along the middle shank 403 and into the distal and proximal threading.

Referring to FIGS. 42-46, there is shown another exemplary form of screw component, generally designated 450, of a bone compression screw for compressing two bone or boney anatomies such as, but not limited to, a bone joint or bone fracture. The screw component 450 may be part of a bone compression screw that uses any one of the various sleeve components described herein. The screw component 450 is fashioned from a known biocompatible implant material.

The screw component 450 is characterized by a body 451 having a distal end 457 with external male bone screw threads or threading 452, a smooth middle shank 453, and a proximal end 456 with a smooth, generally short section 455 and external male machine screw threads or threading 454. The proximal end 456 also includes a peripheral bevel 459. The proximal end 456 and the shank 453 have a first diameter, while the distal end 457 has a second diameter that is greater than the first diameter. As a consequence, the distal threading 452 has a greater diameter than the proximal threading 454. A peripheral angle 461 provides a transition between the proximal and distal ends. The distal end 457 has a peripheral angle 458 that makes the distal end snub shaped with a flat nose. Additionally, first and second notches or thread features 463, 464 are provided in the threads/threading 452. The first and second thread features 463, 464 provide gripping strength to the screw component 450.

Figure 43:
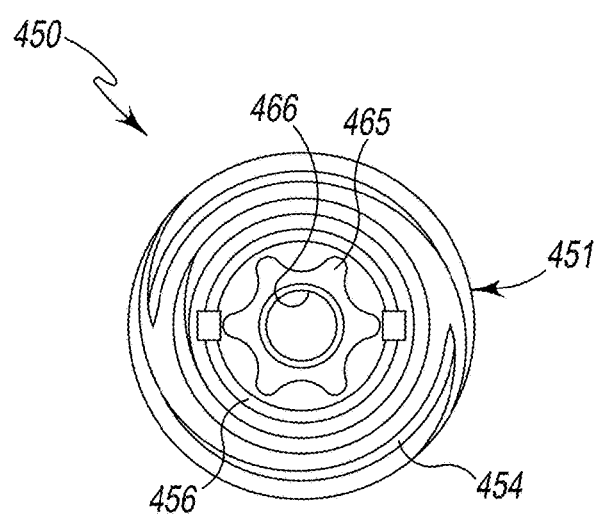
FIG. 43 is an end view of the cannulated screw component of FIG. 42 taken along line 43-43 thereof.
Figure 44:
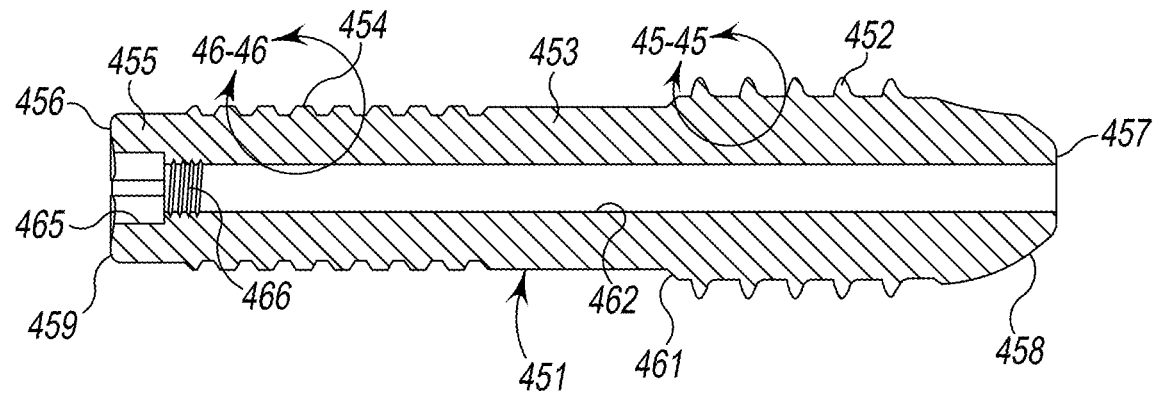
FIG. 44 is a sectional view of the cannulated screw component of FIG. 42 taken along line 44-44 thereof.

In this form, the body 451 is cannulated (has a longitudinal bore) 462 extending through the body 451 from the proximal end 456 to the distal end 457. As seen in FIGS. 43, 44, the proximal end 456 has a configured drive socket 465 at the proximal end opening of the bore 462. The configured drive socket 465 may be hexalobe (hexagonal) shaped to receive a hexalobe driving tool (not shown) such as is known in the art. Of course, other configurations may be used. The bore 462 further includes internal threading 466 axially adjacent to the socket 465, the threading 466 for receiving an installation instrument (not shown).

Figure 45:
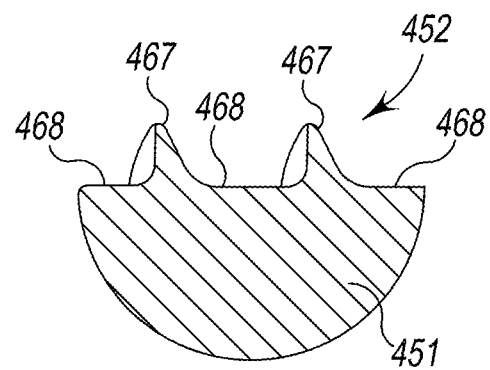
FIG. 45 is an enlarged portion of the cannulated screw component of FIG. 44 taken along circle 45-45 thereof.
Figure 46:
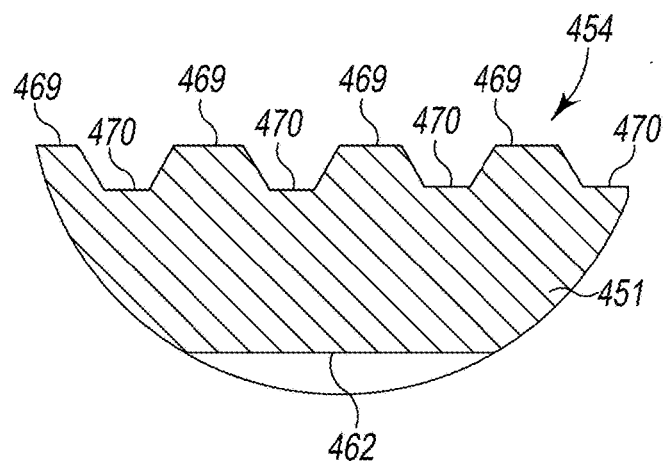
FIG. 46 is an enlarged portion of the cannulated screw component of FIG. 44 taken along circle 46-46 thereof.

FIG. 45 provides an enlarged view of the distal threading 452. The distal threading 452 is characterized by a sharp helical projection 467 winding about the distal end 457. Helical flat 468 is defined between the helical projection 467 and thus likewise forms a spiral path about the distal end. The threading 452 is configured for reception in bone. FIG. 46 provides an enlarged view of the proximal threading 454. The proximal threading 454 is characterized by a flat helical projection 469 winding about the proximal end 456. A helical flat 470 is defined between the helical projection 469 and thus likewise forms a spiral path about the proximal end. The proximal threading 454 is configured to receive the sleeve 430 (see FIGS. 35-41) or the other sleeves described herein.

FIGS. 47-50 shows another exemplary form of a screw component, generally designated 450*a*, of a bone compression screw for compressing two bone or boney anatomies such as, but not limited to, a bone joint or bone fracture. The screw component 450*a* may be part of a bone compression screw that uses any one of the various sleeve components described herein. The screw component 450*a* is fashioned from a known biocompatible implant material.

The screw component 450*a* is characterized by a body 451 having a distal end 457 with external male bone screw threads or threading 452, a smooth middle shank 453, and a proximal end 456 with a smooth section 455 and external male machine screw threads or threading 454. The smooth section 455 has a generally short length. The proximal end 456 also includes a peripheral bevel 459. The proximal end 456 and the shank 453 have a first diameter, while the distal end 457 has a second diameter that is greater than the first diameter. As a consequence, the distal threading 452 has a greater diameter than the proximal threading 454. A peripheral angle 461 provides a transition between the proximal and distal ends. The distal end 457 has a peripheral angle 458 that makes the distal end snub shaped with a flat nose. Additionally, first and second notches or thread features 463, 464 are provided in the threads/threading 452. The first and second thread features 463, 464 provide gripping strength to the screw component 450*a*.

Figure 48:
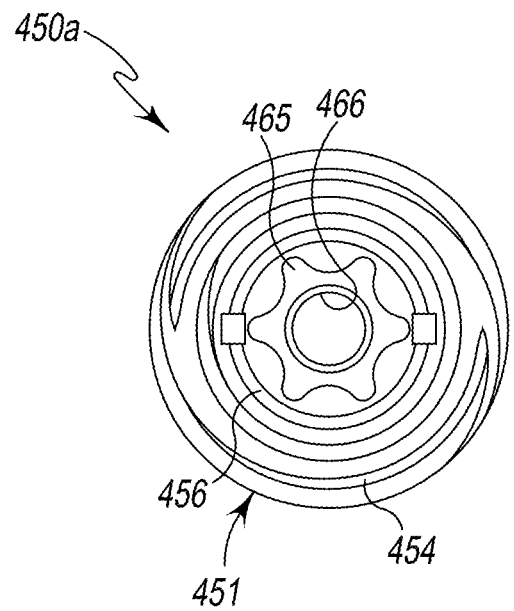
FIG. 48 is an end view of the cannulated and slotted screw component of FIG. 47 taken alone line 49-49 thereof.
Figure 49:
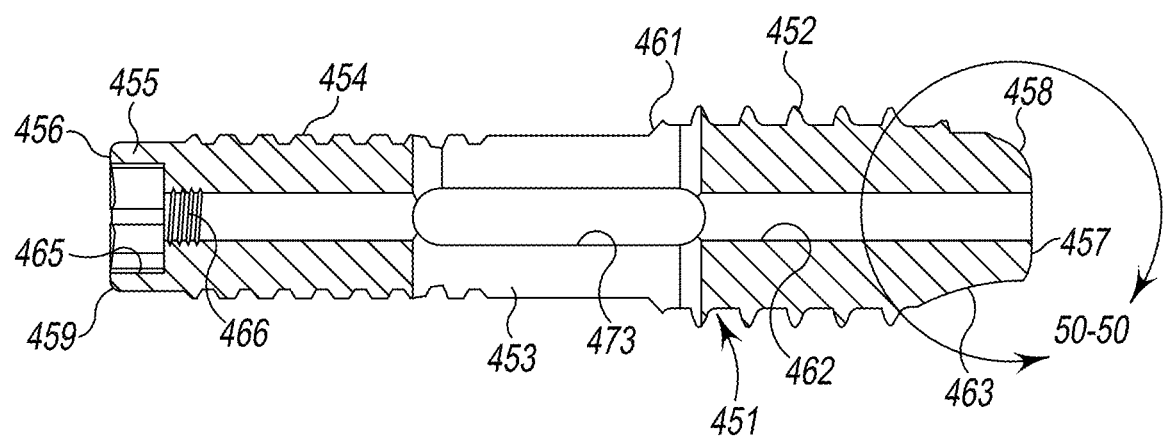
FIG. 49 is a sectional view of the cannulated and slotted screw component of FIG. 47 taken along line 49-49 thereof.

In this form, the body 451 is cannulated (has a longitudinal bore) 462 extending through the body 451 from the proximal end 456 to the distal end 457. As seen in FIGS. 48, 49, the proximal end 456 has a configured drive socket 465 at the proximal end opening of the bore 462. The configured drive socket 465 may be hexalobe (hexagonal) shaped to receive a hexalobe driving tool (not shown) such as is known in the art. Of course, other configurations may be used. The bore 462 further includes internal threading 466 axially adjacent to the socket 415, the threading 466 for receiving an installation instrument (not shown).

Figure 47:
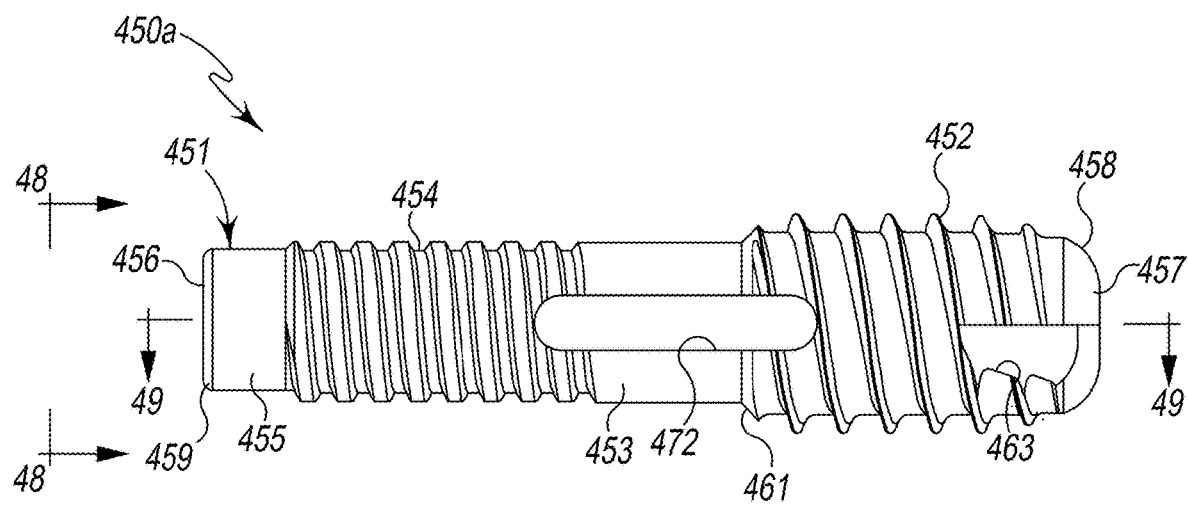
FIG. 47 is a side view another exemplary form of a cannulated and slotted screw component for a bone compression screw fashioned in accordance with the principles of the present invention.
Figure 50:
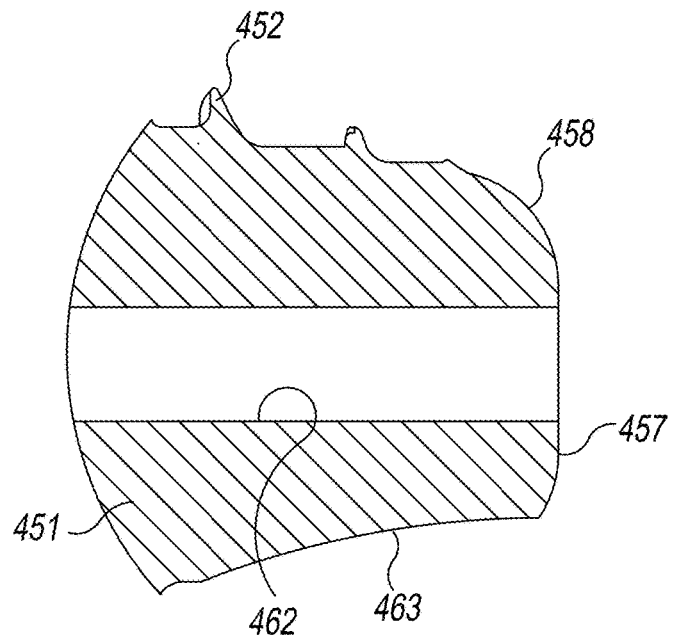
FIG. 50 is an enlarged portion of the cannulated and slotted screw component of FIG. 49 taken along circle 50-50 thereof.

FIG. 50 provides an enlarged view of the distal threading 452. The distal threading 452 is characterized by a sharp helical projection winding about the distal end 457. A helical flat is defined between the helical projection and thus likewise forms a spiral path about the distal end. The threading 452 is configured for reception in bone. While not shown in detail, the proximal threading 454 is characterized by a flat helical projection winding about the proximal end while a helical flat is defined between the helical projection and thus likewise forms a spiral path about the proximal end. The proximal threading is configured to receive the sleeve 430 (see FIGS. 35-41) or the other sleeves described herein. The screw component 450*a* further includes four slots of which two slots 472, 473 are seen in FIGS. 47, 49. The four slots are situated at 90° intervals about the body 451. Each slot extends longitudinally along the middle shank 453 and into the distal and proximal threading.

Figure 51:
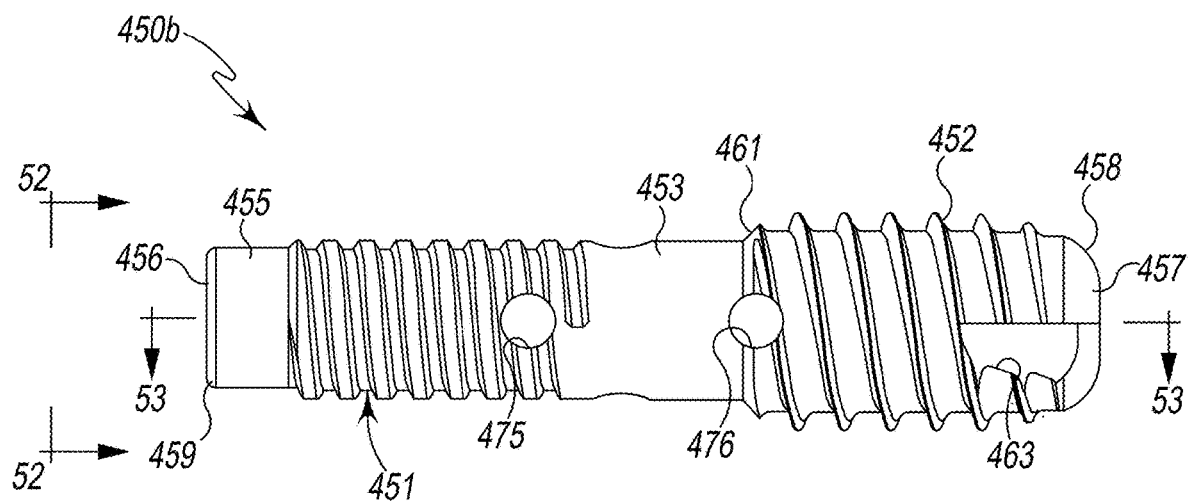
FIG. 51 is a side view of another exemplary form of a cannulated and fenestrated screw component for a bone compression screw fashioned in accordance with the principles of the present invention.
Figure 52:
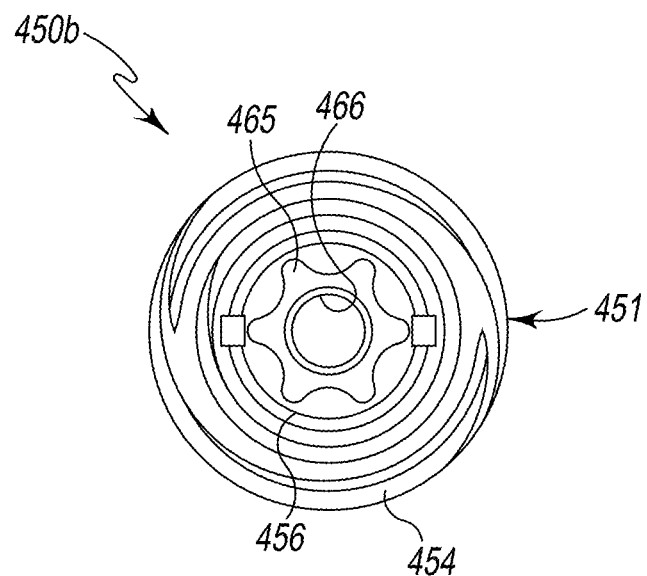
FIG. 52 is an end view of the cannulated and fenestrated screw component of FIG. 51 taken along line 52-52 thereof.
Figure 53:
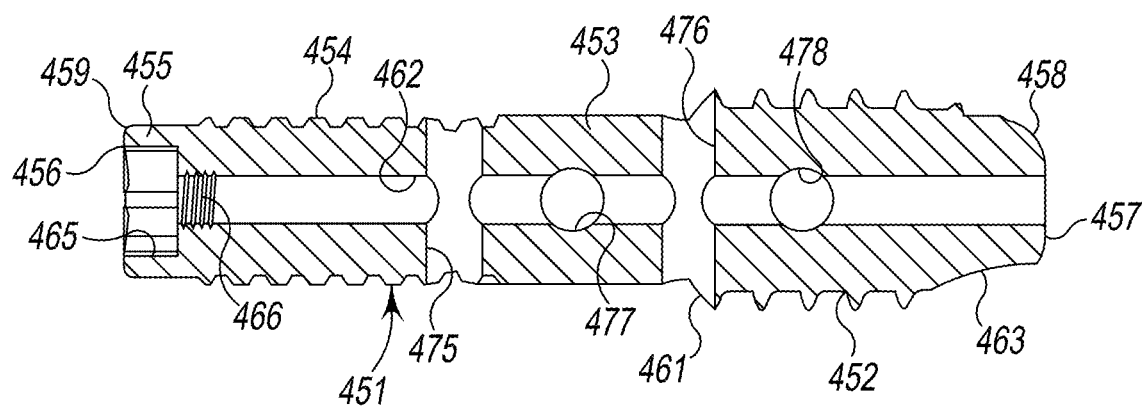
FIG. 53 is a sectional view of the cannulated and fenestrated screw component of FIG. 51 taken along line 53-53 thereof.

FIGS. 51-53 shows another exemplary form of a screw component, generally designated 450*b*, of a bone compression screw for compressing two bone or boney anatomies such as, but not limited to, a bone joint or bone fracture. The screw component 450*b* may be part of a bone compression screw that uses any one of the various sleeve components described herein. The screw component 450*b* is fashioned from a known biocompatible implant material.

The screw component 450*b* is characterized by a body 451 having a distal end 457 with external male bone screw threads or threading 452, a smooth middle shank 453, and a proximal end 456 with a smooth section 455 and external male machine screw threads or threading 454. The smooth section 455 has a generally short length. The proximal end 456 also includes a peripheral bevel 459. The proximal end 456 and the shank 453 have a first diameter, while the distal end 457 has a second diameter that is greater than the first diameter. As a consequence, the distal threading 452 has a greater diameter than the proximal threading 454. A peripheral angle 461 provides a transition between the proximal and distal ends. The distal end 457 has a peripheral angle 458 that makes the distal end snub shaped with a flat nose. Additionally, first and second notches or thread features 463, 464 are provided in the threads/threading 452. The first and second thread features 463, 464 provide gripping strength to the screw component 450*b*.

In this form, the body 451 is cannulated (has a longitudinal bore) 462 extending through the body 451 from the proximal end 456 to the distal end 457. As seen in FIGS. 52, 53, the proximal end 456 has a configured drive socket 465 at the proximal end opening of the bore 462. The configured drive socket 465 may be hexalobe (hexagonal) shaped to receive a hexalobe driving tool (not shown) such as is known in the art. Of course, other configurations may be used. The bore 462 further includes internal threading 466 axially adjacent to the socket 415, the threading 466 for receiving an installation instrument (not shown).

While not shown in detail, the distal threading 452 is characterized by a sharp helical projection winding about the distal end 457. A helical flat is defined between the helical projection and thus likewise forms a spiral path about the distal end. The threading 452 is configured for reception in bone. While again not shown in detail, the proximal threading 454 is characterized by a flat helical projection winding about the proximal end while a helical flat is defined between the helical projection and thus likewise forms a spiral path about the proximal end. The proximal threading is configured to receive the sleeve 430 (see FIGS. 35-41) or the other sleeves described herein. The screw component 450*a* further includes four through-holes or bores 475, 476, 477, and 478. Two of the four through-holes are situated 90° to the other two through-holes and in a staggered relationship.

Referring to FIGS. 35-41, the sleeve component 430 is shown that may be used with all of the various screw components described herein. The sleeve component 430 is characterized by a body 431 having external male bone screw threads or threading 432 with a thread pitch that is equal to, smaller than, or larger than the thread pitch of the external male bone screw threads of any screw components. The body 432 further has a bore 439 that extends the length of the body 432 and is sized to be received over and onto the proximal end of any screw component. The body 432 further has internal female machine screw threads or threading 440 in the bore 439 that are/is configured to mate with the external male machine screw threads/threading of the proximal end of any screw component. The body 432 further has a head 433 with two notches 435, 436. The two notches 435, 436 are disposed in the head 432 opposite one another and allow a driving tool to engage and independently drive the sleeve component 430 relative to any screw component. While two notches 435, 436 are shown, the head 433 may have more than two notches if desired.

Figure 38:
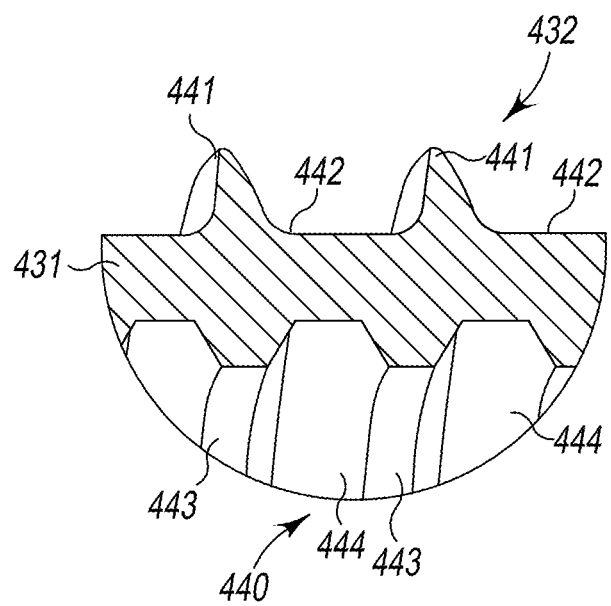
FIG. 38 is an enlarged portion of the sleeve component of FIG. 37 taken along line 38-38 thereof.
Figure 39:
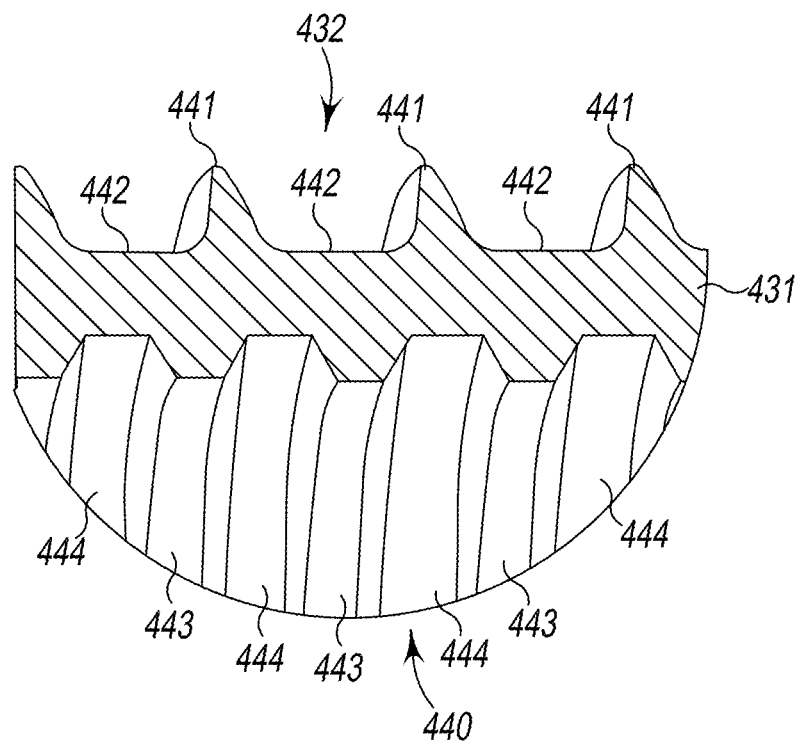
FIG. 39 is an enlarged portion of the sleeve component of FIG. 37 taken along circle 37-37 thereof.
Figure 40:
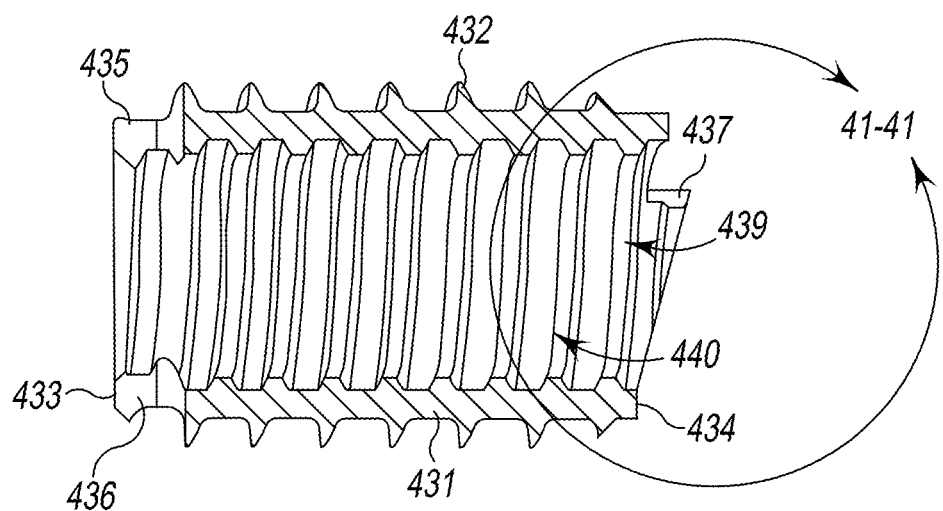
FIG. 40 is a sectional view of the sleeve component of FIG. 35 taken along circle 40-40 thereof.
Figure 41:
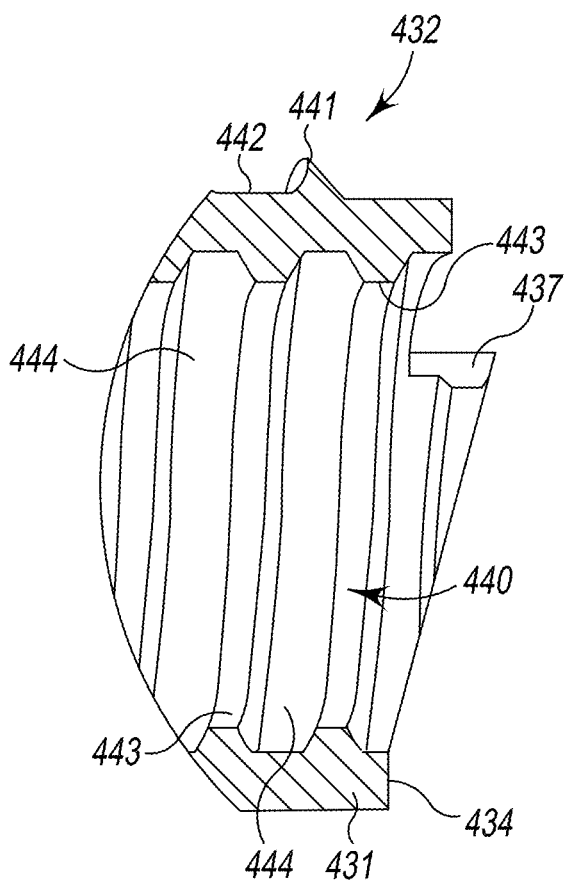
FIG. 41 is an enlarged portion of the sleeve component of FIG. 40 taken along circle 41-41 thereof.
Figure 42:
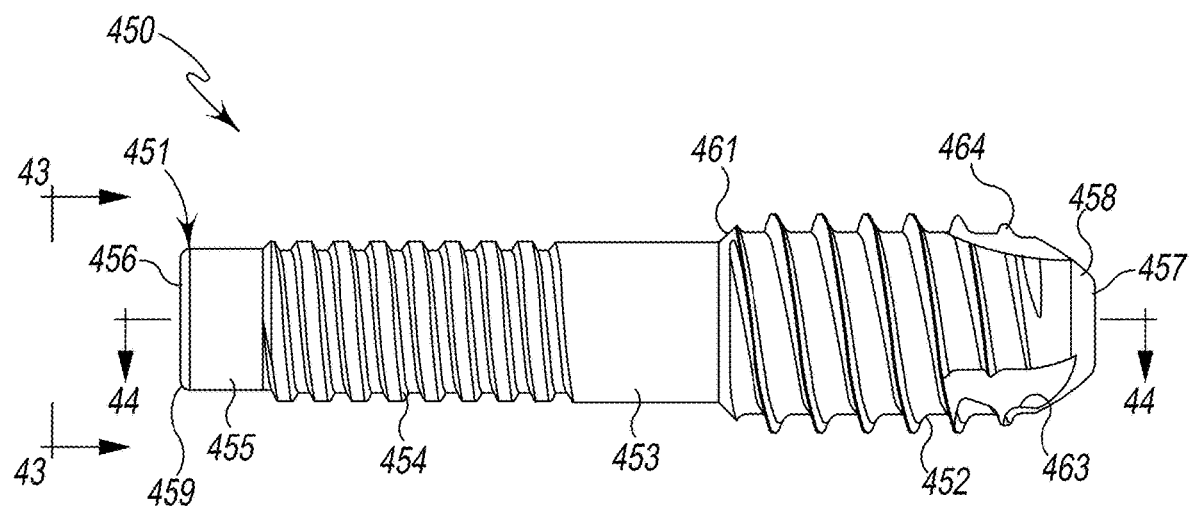
FIG. 42 is a side view of another exemplary form of a cannulated screw component for a bone compression screw fashioned in accordance with the principles of the present invention.

FIGS. 38, 39 provides two enlarged views of the external threading 432 of the sleeve component 430. The external threading 432 is characterized by a sharp helical projection 441 winding about the length of the body 431 of the sleeve component 430. Helical flat 442 is defined between the helical projection 441 and thus likewise forms a spiral path about the length of the body 431 of the sleeve component 430. The threading 432 is configured for reception in bone. FIGS. 38 and 39 also provides an enlarged view of the internal threading 440 of the sleeve component 430. The internal threading 440 is characterized by a flat helical projection 443 winding about the bore 439. A helical flat 444 is defined between the helical projection 443 and thus likewise forms a spiral path about the bore 439. The internal threading 440 is configured to receive the proximal external threading of the screw components described herein. As best seen in FIGS. 35, 37, 40, 41, one end 434 of the body 431 of the sleeve component 430 has two teeth 437, 438 that provide starting points of the threading of the sleeve.

Figure 54:
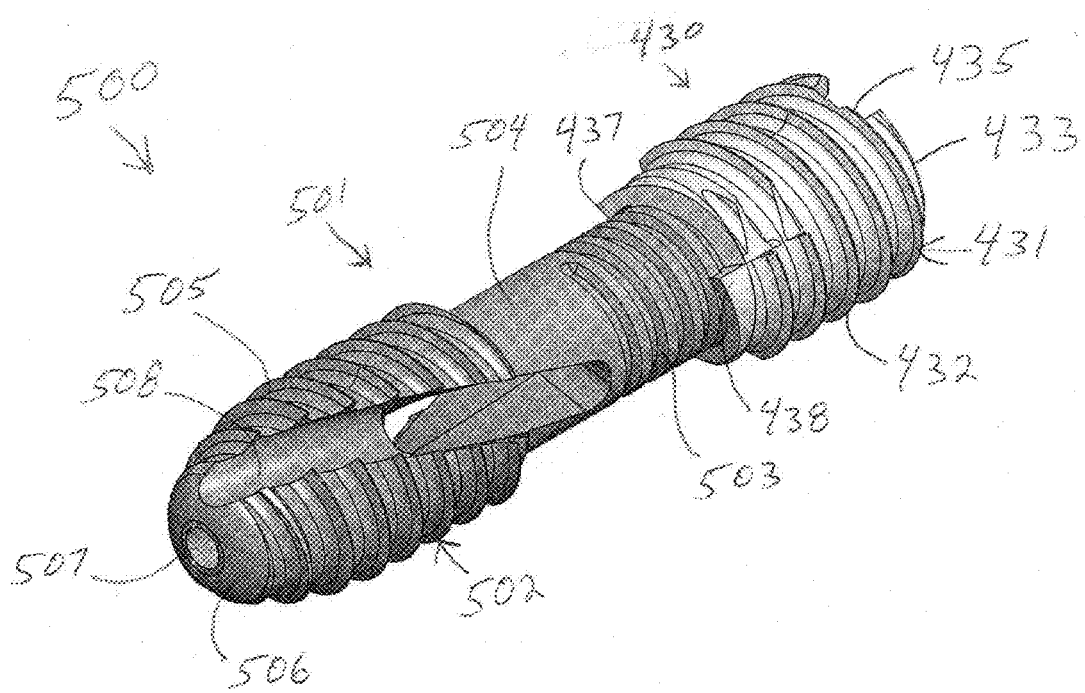
FIG. 54 is an isometric view of an exemplary form of a bone compression screw having bone cutting flutes with slots fashioned in accordance with the principles of the present invention.
Figure 55:
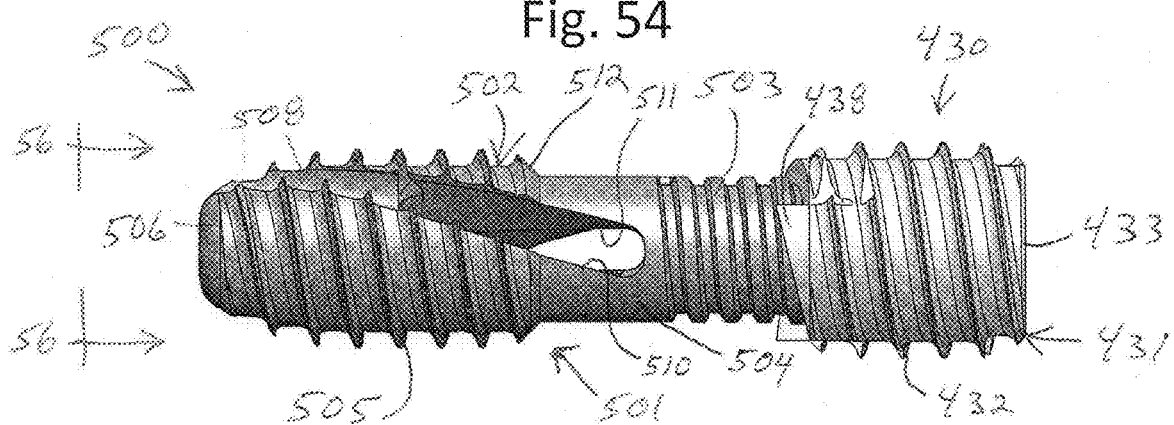
FIG. 55 is a side view of the bone compression screw of FIG. 54.
Figure 56:
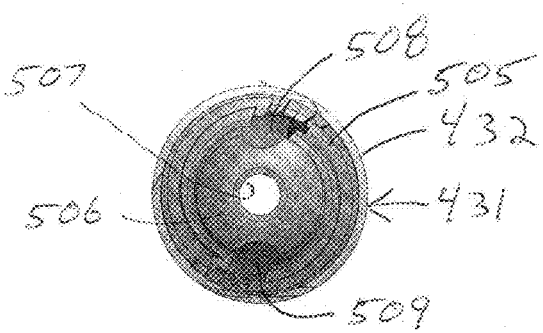
FIG. 56 is an end view of the bone compression screw of FIG. 55 taken along line 56-56 thereof.

Referring to FIGS. 54-56, there is depicted another exemplary embodiment of a bone compression screw, generally designated 500, for compressing two bone or boney anatomies such as, but not limited to, a bone joint or bone fracture. The bone compression screw 500 comprises a screw component 501 and the sleeve component 430 as described above and, as such, will not be described again with respect to the bone compression screw 500. The screw component 501 is fashioned from a known biocompatible implant material.

The screw component 501 is characterized by a body 502 having a distal end with external male bone screw threading 505, a smooth middle shank 504, and a proximal end with external male machine screw threading 503. In this form, the body 502 is cannulated/has a longitudinal bore 507 extending from an angled nose 506 of the distal end to the proximal end (not seen). While not seen in the figures, the proximal end has a hexalobe/hexagon shaped socket to receive a hexalobe/hexagonal driving tool (not shown) such as is known in the art. Of course, other socket configurations may be used.

While not seen, the proximal end also preferably, but not necessarily, includes a peripheral bevel. The proximal threaded end 503 and the middle shank 504 have a first diameter, while the distal threaded end 505 has a second diameter that is greater than the first diameter. As a consequence, the distal threading 505 has a greater diameter than the proximal threading 503. A peripheral angle 512 provides a transition between the proximal and distal ends.

While not shown in detail, the distal threading 508 is characterized by a sharp helical projection winding about the distal end. A helical flat is defined between the helical projection and thus likewise forms a spiral path about the distal end. The threading 508 is configured for reception in bone. While again not shown in detail, the proximal threading 503 is characterized by a flat helical projection winding about the proximal end while a helical flat is defined between the helical projection and thus likewise forms a spiral path about the proximal end. The proximal threading is configured to receive the sleeve 430 (see FIGS. 35-41) or the other sleeves described herein.

The screw component 501 further includes a first flute 508 that extends from the nose 506 of the distal end into the middle section 504. The first flute 508 has a slight helical geometry along the longitudinal periphery of the body 502. A second flute 509 is provided in the body 502 opposite to the first flute 508, the nomenclature first and second being arbitrary. The second flute 509 has a slight helical geometry along the longitudinal periphery of the body 502. The helical flutes function as bone cutting flutes that self-harvest bone graft during installation that is collected by graft windows of the screw component body 502. The graft windows of the screw component 501 comprise a first slot 510 for and of the first flute 508 (which is perpendicular to the long axis or bore 506 of the screw component 501), and a second slot 511 for and of the second flute 509 (which is perpendicular to the long axis or bore 506 of the screw component 501), the nomenclature first and second being arbitrary. The method of installation of the bone compression screw 500 is as described above.

Figure 57:
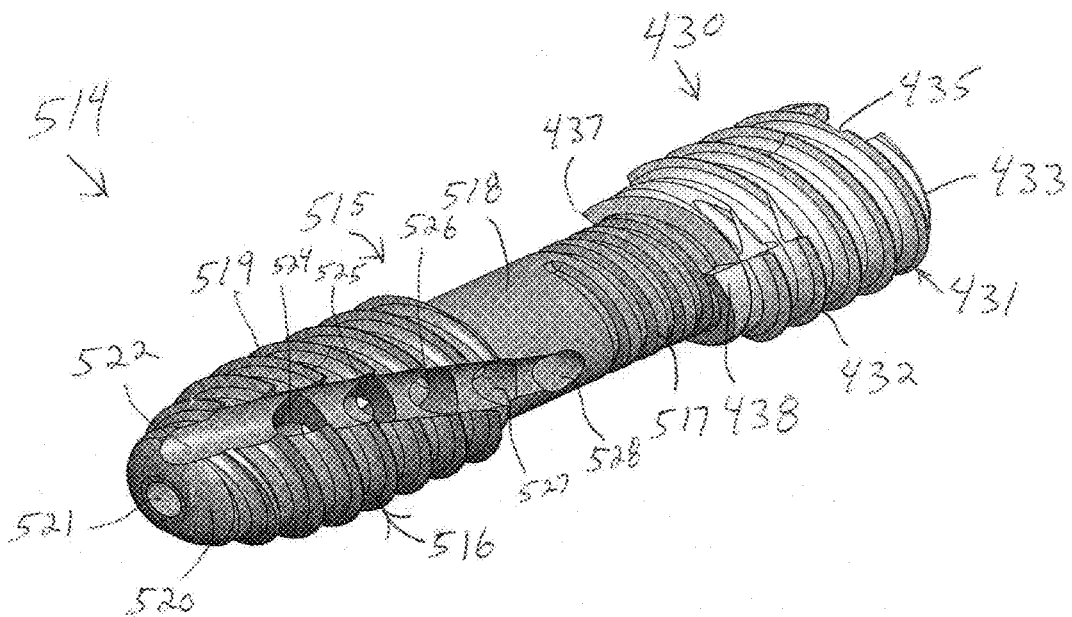
FIG. 57 is an isometric view of an exemplary form of a bone compression screw having bone cutting flutes with fenestrated holes fashioned in accordance with the principles of the present invention.
Figure 58:
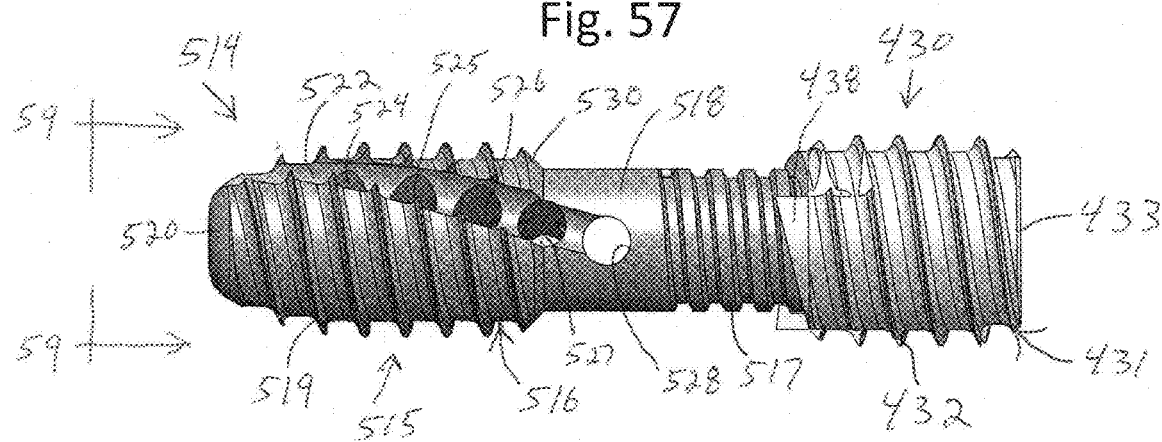
FIG. 58 is a side view of the bone compression screw of FIG. 57.
Figure 59:
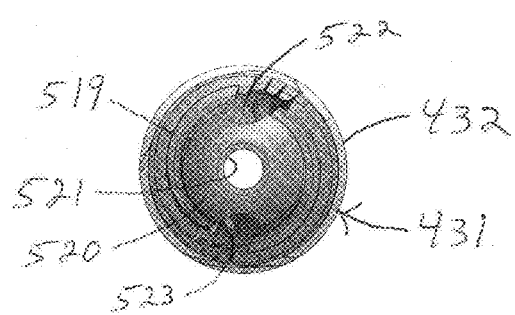
FIG. 59 is an end view of the bone compression screw of FIG. 58 taken along line 59-59 thereof.

Referring to FIGS. 57-59, there is depicted another exemplary embodiment of a bone compression screw, generally designated 514, for compressing two bone or boney anatomies such as, but not limited to, a bone joint or bone fracture. The bone compression screw 514 comprises a screw component 515 and the sleeve component 430 as described above and, as such, will not be described again with respect to the bone compression screw 514. The screw component 515 is fashioned from a known biocompatible implant material.

The screw component 515 is characterized by a body 516 having a distal end with external male bone screw threading 519, a smooth middle shank 518, and a proximal end with external male machine screw threading 517. In this form, the body 516 is cannulated/has a longitudinal bore 521 extending from an angled nose 520 of the distal end to the proximal end (not seen). While not seen in the figures, the proximal end has a hexalobe/hexagon shaped socket to receive a hexalobe/hexagonal driving tool (not shown) such as is known in the art. Of course, other socket configurations may be used.

While not seen, the proximal end also preferably, but not necessarily, includes a peripheral bevel. The proximal threaded end 517 and the middle shank 518 have a first diameter, while the distal threaded end 519 has a second diameter that is greater than the first diameter. As a consequence, the distal threading 519 has a greater diameter than the proximal threading 517. A peripheral angle 530 provides a transition between the proximal and distal ends.

While not shown in detail, the distal threading 519 is characterized by a sharp helical projection winding about the distal end. A helical flat is defined between the helical projection and thus likewise forms a spiral path about the distal end. The threading 519 is configured for reception in bone. While again not shown in detail, the proximal threading 517 is characterized by a flat helical projection winding about the proximal end while a helical flat is defined between the helical projection and thus likewise forms a spiral path about the proximal end. The proximal threading is configured to receive the sleeve 430 (see FIGS. 35-41) or the other sleeves described herein.

The screw component 515 further includes a first flute 522 that extends from the nose 520 of the distal end into the middle section 518. The first flute 522 has a slight helical geometry along the longitudinal periphery of the body 516. A second flute 523 is provided in the body 516 opposite to the first flute 522, the nomenclature first and second being arbitrary. The second flute 523 has a slight helical geometry along the longitudinal periphery of the body 516. The helical flutes function as bone cutting flutes that self-harvest bone graft during installation that is collected by graft windows of the screw component body 516. The graft windows of the screw component 515 comprise a plurality of circular fenestrae 524, 525, 526, 527, 528, each one of which extends perpendicular to the longitudinal axis/bore 521 of the body 516 and are spaced along and between the first and second flutes 522, 523. More or less circular fenestrae may be provided. Additionally, the fenestrae may have shapes other than circular. The method of installation of the bone compression screw 500 is as described above.

It should be appreciated that dimensions of the various bone compression screws' components and/or features can be altered as desired.

What is claimed is:

1. A bone compression screw configured to be implanted by a driving tool, the bone compression screw comprising:
    a screw component having a proximal end, a proximal section adjacent the proximal end, a distal end, a distal section adjacent the distal end, and a middle section between the proximal section and the distal section; and
    a sleeve component having a central bore extending from a first end to a second end;
    wherein the proximal section of the screw component includes a first machine screw threading and a smooth non-threaded section on the exterior of the screw component between the first threading and the proximal end,
    wherein the distal section of the screw component includes a first bone screw threading, the first machine screw threading defining a first diameter and the first bone screw threading defining a second diameter, wherein the first diameter is less than the second diameter; and
    wherein the middle section of the screw component includes a non-threaded surface that provides a transition between the proximal section and the distal section;
    wherein the sleeve component includes a head, a second machine screw threading on an inside surface of the central bore, and a second bone screw threading on an outside surface of the sleeve component, wherein the second machine screw threading is configured to be received on the first machine screw threading of the proximal section of the screw component, wherein the head includes one or more notches configured to be engaged by the driving tool, and wherein the notches on the sleeve are substantially aligned with the smooth non-threaded section of the screw component when the sleeve is mated with the screw component.

2. The bone compression screw of claim 1, wherein the first threading of the proximal section of the screw component and the third threading of the sleeve component are machine screw threading, and the first threading of the distal section of the screw component and the fourth threading of the sleeve component are bone screw threading.

3. The bone compression screw of claim 2, wherein the screw component includes a longitudinal bore extending through the proximal section, the middle section, and the distal section.

4. The bone compression screw of claim 3, wherein the screw component has one or more fenestrae holes extending transverse to the longitudinal bore.

5. The bone compression screw of claim 1, wherein the distal section includes a peripheral angled surface to provide a flat end surface.

* * * * *